US012055485B2

(12) United States Patent
Smith et al.

(10) Patent No.: US 12,055,485 B2
(45) Date of Patent: Aug. 6, 2024

(54) MULTISPECIES MEASUREMENT PLATFORM USING ABSORPTION SPECTROSCOPY FOR MEASUREMENT OF CO-EMITTED TRACE GASES

(71) Applicant: SeekOps Inc., Austin, TX (US)

(72) Inventors: Brendan James Smith, Lakeway, TX (US); Iain Michael Cooper, Canyon Lake, TX (US)

(73) Assignee: SeekOps Inc., Austin, TX (US)

(*) Notice: Subject to any disclaimer, the term of this patent is extended or adjusted under 35 U.S.C. 154(b) by 29 days.

(21) Appl. No.: 17/394,130

(22) Filed: Aug. 4, 2021

(65) Prior Publication Data

US 2021/0364427 A1 Nov. 25, 2021

Related U.S. Application Data

(63) Continuation-in-part of application No. PCT/US2021/016821, filed on Feb. 5, 2021.

(60) Provisional application No. 63/170,303, filed on Apr. 2, 2021, provisional application No. 62/970,329, filed on Feb. 5, 2020.

(51) Int. Cl.
*G01N 21/39* (2006.01)
*G01N 33/00* (2006.01)

(52) U.S. Cl.
CPC ....... *G01N 21/39* (2013.01); *G01N 2021/391* (2013.01); *G01N 33/004* (2013.01); *G01N 33/0047* (2013.01); *G01N 2201/0612* (2013.01); *G01N 2201/062* (2013.01)

(58) Field of Classification Search
CPC .. G01N 21/39; G01N 33/004; G01N 33/0047; G01N 2021/391; G01N 2201/0612; G01N 2201/062; G01N 2201/0214; G01N 2201/0216; G01N 2201/0221; G01N 21/3504; G01N 21/031;
(Continued)

(56) References Cited

U.S. PATENT DOCUMENTS 3,780,566 A 12/1973 Smith et al.
4,135,092 A 1/1979 Milly
(Continued)

FOREIGN PATENT DOCUMENTS

AU 3401499 A 11/1999
CN 104458588 A 3/2015
(Continued)

OTHER PUBLICATIONS

International Search Report and Written Opinion for PCT/US22/38951, mailed Nov. 28, 2022.
(Continued)

*Primary Examiner* — Md M Rahman
(74) *Attorney, Agent, or Firm* — Concept IP LLP; Michael Zarrabian

(57) ABSTRACT

Systems, devices, and methods including one or more optical cavities; one or more light sources configured to emit a specified wavelength or band of wavelengths of light; and one or more photovoltaic detectors configured to receive the emitted light that has traveled over one or more path lengths, where the one or more photovoltaic detectors are configured to detect at least one of: a first trace gas species and a second trace gas species.

12 Claims, 32 Drawing Sheets

(58) Field of Classification Search
CPC ...... G01N 2021/399; G01N 2201/1293; G01J 3/433; Y02A 50/20
USPC ........................................................ 356/437
See application file for complete search history.

(56) References Cited

U.S. PATENT DOCUMENTS

| | | | |
|---|---|---|---|
| 4,233,564 A | 11/1980 | Kerbel | |
| 4,507,558 A | 3/1985 | Bonne | |
| 4,988,833 A | 1/1991 | Lai | |
| 5,047,639 A | 9/1991 | Wong | |
| 5,075,619 A | 12/1991 | Said | |
| 5,173,749 A | 12/1992 | Tell et al. | |
| 5,291,265 A | 3/1994 | Kebabian | |
| 5,317,156 A | 5/1994 | Cooper et al. | |
| 5,767,780 A | 6/1998 | Smith et al. | |
| 5,822,058 A | 10/1998 | Adler-Golden et al. | |
| 6,064,488 A | 5/2000 | Brand et al. | |
| 6,295,859 B1 | 10/2001 | Hayden et al. | |
| 6,356,350 B1 | 3/2002 | Silver et al. | |
| 6,509,566 B1 | 1/2003 | Wamsley et al. | |
| 6,549,630 B1 | 4/2003 | Bobisuthi | |
| 7,800,751 B1 | 9/2010 | Silver et al. | |
| 7,833,480 B2 | 11/2010 | Blazewicz et al. | |
| 8,060,270 B2 | 11/2011 | Vian et al. | |
| 8,294,899 B2 | 10/2012 | Wong | |
| 8,451,120 B2 | 5/2013 | Johnson, Jr. et al. | |
| 8,730,461 B2 | 5/2014 | Andreussi | |
| 9,183,371 B2 | 11/2015 | Narendra et al. | |
| 9,183,731 B1 | 11/2015 | Bokhary | |
| 9,235,974 B2 | 1/2016 | Johnson, Jr. et al. | |
| 9,250,175 B1 | 2/2016 | McManus | |
| 9,494,511 B2 | 11/2016 | Wilkins | |
| 9,599,529 B1 | 3/2017 | Steele et al. | |
| 9,599,597 B1 | 3/2017 | Steele et al. | |
| 10,023,311 B2 | 7/2018 | Lai et al. | |
| 10,023,323 B1 | 7/2018 | Roberts et al. | |
| 10,031,040 B1 | 7/2018 | Smith et al. | |
| 10,126,200 B1 | 11/2018 | Steele et al. | |
| 10,268,198 B2 | 4/2019 | Mantripragada et al. | |
| 10,325,485 B1 | 6/2019 | Schuster | |
| 10,365,646 B1 | 7/2019 | Farnsworth et al. | |
| 10,429,546 B1 | 10/2019 | Ulmer | |
| 10,677,771 B2 | 6/2020 | Dittberner et al. | |
| 10,753,864 B2 | 8/2020 | Kasten et al. | |
| 10,816,458 B2 | 10/2020 | Kasten et al. | |
| 10,830,034 B2 | 11/2020 | Cooley et al. | |
| 10,962,437 B1 | 3/2021 | Nottrott et al. | |
| 11,105,784 B2 | 8/2021 | Kukreja et al. | |
| 11,112,308 B2 | 9/2021 | Kreitinger et al. | |
| 11,275,068 B2 | 3/2022 | Willett | |
| 11,299,268 B2 | 4/2022 | Christensen et al. | |
| 11,519,855 B2 | 12/2022 | Black et al. | |
| 11,557,212 B2 | 1/2023 | Hong | |
| 11,614,430 B2 | 3/2023 | Buckingham et al. | |
| 11,619,562 B2 | 4/2023 | Leen et al. | |
| 11,710,411 B2 | 7/2023 | Van Meeteren et al. | |
| 11,748,866 B2 | 9/2023 | Vargas | |
| 2002/0005955 A1* | 1/2002 | Kramer | G01J 9/0246 356/519 |
| 2003/0160174 A1 | 8/2003 | Grant et al. | |
| 2003/0189711 A1 | 10/2003 | Orr et al. | |
| 2003/0230716 A1 | 12/2003 | Russell et al. | |
| 2004/0012787 A1 | 1/2004 | Galle et al. | |
| 2004/0017762 A1 | 1/2004 | Sogawa et al. | |
| 2004/0212804 A1 | 10/2004 | Neff et al. | |
| 2006/0015290 A1 | 1/2006 | Warburton et al. | |
| 2006/0044562 A1 | 3/2006 | Hagene et al. | |
| 2006/0232772 A1 | 10/2006 | Silver | |
| 2006/0234621 A1 | 10/2006 | Desrochers et al. | |
| 2007/0137318 A1 | 6/2007 | Desrochers et al. | |
| 2008/0169934 A1 | 7/2008 | Lang et al. | |
| 2008/0243372 A1 | 10/2008 | Bodin et al. | |
| 2009/0201507 A1 | 8/2009 | Kluczynski et al. | |
| 2009/0263286 A1 | 10/2009 | Isomura et al. | |
| 2009/0326792 A1 | 12/2009 | McGrath | |
| 2010/0004798 A1 | 1/2010 | Bodin et al. | |
| 2010/0131207 A1 | 5/2010 | Lippert et al. | |
| 2010/0140478 A1 | 6/2010 | Wilson et al. | |
| 2010/0147081 A1 | 6/2010 | Thomas | |
| 2011/0035149 A1 | 2/2011 | McAndrew et al. | |
| 2011/0074476 A1 | 3/2011 | Heer et al. | |
| 2011/0150035 A1 | 6/2011 | Hanson et al. | |
| 2011/0164251 A1 | 7/2011 | Richter | |
| 2011/0213554 A1 | 9/2011 | Archibald et al. | |
| 2011/0242659 A1 | 10/2011 | Eckles et al. | |
| 2011/0257944 A1 | 10/2011 | Du et al. | |
| 2012/0120397 A1 | 5/2012 | Furtaw et al. | |
| 2013/0044314 A1 | 2/2013 | Koulikov et al. | |
| 2013/0076900 A1 | 3/2013 | Mrozek et al. | |
| 2013/0208262 A1 | 8/2013 | Andreussi | |
| 2014/0172323 A1 | 6/2014 | Marino | |
| 2014/0204382 A1 | 7/2014 | Christensen | |
| 2014/0236390 A1 | 11/2014 | Mohamadi | |
| 2014/0336957 A1 | 11/2014 | Hanson et al. | |
| 2015/0072633 A1 | 3/2015 | Massarella et al. | |
| 2015/0145954 A1 | 5/2015 | Pulleti et al. | |
| 2015/0275114 A1* | 10/2015 | Tumiatti | C10L 3/00 435/170 |
| 2015/0295543 A1 | 10/2015 | Brown et al. | |
| 2015/0316473 A1 | 11/2015 | Kester et al. | |
| 2015/0323449 A1 | 11/2015 | Jones et al. | |
| 2015/0336667 A1 | 11/2015 | Srivastava et al. | |
| 2016/0018373 A1 | 1/2016 | Pagé et al. | |
| 2016/0070265 A1 | 3/2016 | Liu et al. | |
| 2016/0104250 A1 | 4/2016 | Allen et al. | |
| 2016/0146696 A1 | 5/2016 | Steele et al. | |
| 2016/0161456 A1* | 6/2016 | Risk | G01P 5/06 702/24 |
| 2016/0202225 A1 | 7/2016 | Feng et al. | |
| 2016/0214715 A1 | 7/2016 | Meffert | |
| 2016/0307447 A1 | 10/2016 | Johnson et al. | |
| 2016/0357192 A1 | 12/2016 | McGrew et al. | |
| 2017/0003684 A1 | 1/2017 | Knudsen et al. | |
| 2017/0057071 A1 | 3/2017 | Krohne et al. | |
| 2017/0089829 A1* | 3/2017 | Bartholomew | G01S 7/499 |
| 2017/0093122 A1 | 3/2017 | Bean et al. | |
| 2017/0097274 A1 | 4/2017 | Thorpe et al. | |
| 2017/0115218 A1 | 4/2017 | Huang et al. | |
| 2017/0134497 A1 | 5/2017 | Harter et al. | |
| 2017/0158353 A1 | 6/2017 | Schmick | |
| 2017/0199647 A1 | 7/2017 | Richman et al. | |
| 2017/0206648 A1 | 7/2017 | Marra et al. | |
| 2017/0235018 A1 | 8/2017 | Foster et al. | |
| 2017/0259920 A1 | 9/2017 | Lai et al. | |
| 2017/0307519 A1 | 10/2017 | Black et al. | |
| 2017/0336281 A1 | 11/2017 | Waxman et al. | |
| 2017/0339820 A1 | 11/2017 | Foster et al. | |
| 2018/0023974 A1 | 1/2018 | Otani et al. | |
| 2018/0045561 A1 | 2/2018 | Leen et al. | |
| 2018/0045596 A1 | 2/2018 | Prasad et al. | |
| 2018/0050798 A1 | 2/2018 | Kapuria | |
| 2018/0059003 A1 | 3/2018 | Jourdainne et al. | |
| 2018/0067066 A1 | 3/2018 | Giedd et al. | |
| 2018/0109767 A1 | 4/2018 | Li et al. | |
| 2018/0122246 A1 | 5/2018 | Clark | |
| 2018/0127093 A1 | 5/2018 | Christensen et al. | |
| 2018/0188129 A1 | 7/2018 | Choudhury et al. | |
| 2018/0259955 A1 | 9/2018 | Noto | |
| 2018/0266241 A1 | 9/2018 | Ferguson et al. | |
| 2018/0266946 A1 | 9/2018 | Kotidis et al. | |
| 2018/0209902 A1 | 10/2018 | Myshak et al. | |
| 2018/0284088 A1 | 10/2018 | Verbeck, IV | |
| 2018/0292374 A1 | 10/2018 | Dittberner et al. | |
| 2018/0321692 A1 | 11/2018 | Castillo-Effen et al. | |
| 2018/0322699 A1 | 11/2018 | Gray et al. | |
| 2019/0011920 A1 | 1/2019 | Heinonen et al. | |
| 2019/0011935 A1 | 1/2019 | Ham et al. | |
| 2019/0025199 A1 | 1/2019 | Koulikov | |
| 2019/0033194 A1 | 1/2019 | DeFreez et al. | |
| 2019/0049364 A1 | 2/2019 | Rubin | |
| 2019/0077506 A1 | 3/2019 | Shaw et al. | |
| 2019/0086202 A1 | 3/2019 | Guan et al. | |
| 2019/0095687 A1 | 3/2019 | Shaw et al. | |

(56) References Cited

U.S. PATENT DOCUMENTS

| | | |
|---|---|---|
| 2019/0154874 A1 | 5/2019 | Shams et al. |
| 2019/0178743 A1 | 6/2019 | McNeil |
| 2019/0195789 A1 | 6/2019 | Pan et al. |
| 2019/0204189 A1 | 7/2019 | Mohr, Jr. et al. |
| 2019/0212419 A1 | 7/2019 | Jeong et al. |
| 2019/0220019 A1 | 7/2019 | Tan et al. |
| 2019/0228573 A1 | 7/2019 | Sen et al. |
| 2019/0234868 A1 | 8/2019 | Tanomura et al. |
| 2019/0331652 A1 | 10/2019 | Ba et al. |
| 2020/0050189 A1 | 2/2020 | Gu et al. |
| 2020/0109976 A1 | 4/2020 | Ajay et al. |
| 2020/0135036 A1 | 4/2020 | Campbell |
| 2020/0249092 A1 | 8/2020 | Podmore et al. |
| 2020/0400635 A1 | 12/2020 | Potyrailo et al. |
| 2021/0017926 A1 | 1/2021 | Alkadi et al. |
| 2021/0037197 A1 | 2/2021 | Kester et al. |
| 2021/0055180 A1 | 2/2021 | Thorpe et al. |
| 2021/0109074 A1 | 4/2021 | Smith et al. |
| 2021/0140934 A1 | 5/2021 | Smith et al. |
| 2021/0190745 A1 | 6/2021 | Buckingham et al. |
| 2021/0190918 A1 | 6/2021 | Li et al. |
| 2021/0199565 A1 | 7/2021 | John et al. |
| 2021/0247369 A1 | 8/2021 | Nottrott et al. |
| 2021/0255158 A1 | 8/2021 | Smith et al. |
| 2021/0300591 A1 | 9/2021 | Tian |
| 2021/0321174 A1 | 10/2021 | Sun et al. |
| 2021/0364427 A1 | 11/2021 | Smith et al. |
| 2021/0382475 A1 | 12/2021 | Smith et al. |
| 2022/0082495 A1 | 3/2022 | Kreitinger et al. |
| 2022/0113290 A1 | 4/2022 | Smith et al. |
| 2022/0268952 A1 | 8/2022 | Liang et al. |
| 2022/0341806 A1 | 10/2022 | Miller et al. |
| 2022/0357231 A1 | 11/2022 | Nahata et al. |
| 2023/0146441 A1 | 5/2023 | Donnat et al. |
| 2023/0160789 A1 | 5/2023 | Donnat et al. |
| 2023/0194487 A1 | 6/2023 | Buckingham et al. |
| 2023/0207070 A1 | 6/2023 | Donnat et al. |
| 2023/0213413 A1 | 7/2023 | Mohr, Jr. et al. |
| 2023/0274651 A1 | 8/2023 | McGuire et al. |
| 2023/0392498 A1 | 12/2023 | Srivastav et al. |

FOREIGN PATENT DOCUMENTS

| | | |
|---|---|---|
| CN | 205749271 U | 11/2016 |
| CN | 109780452 A | 5/2019 |
| CN | 211508182 U | 9/2020 |
| CN | 112213443 A | 1/2021 |
| DE | 29601472 U1 | 5/1996 |
| DE | 69333010 | 4/2004 |
| DE | 102014013822 A1 | 3/2016 |
| DE | 107703075 A | 2/2018 |
| EP | 0450809 A2 | 10/1991 |
| EP | 1371962 B1 | 7/2011 |
| FR | 3047073 B1 | 8/2019 |
| GB | 2538563 A | 11/2016 |
| IN | 106769977 A | 5/2017 |
| JP | H08247939 A | 9/1996 |
| JP | 200975823 A | 4/2009 |
| KR | 20170062813 A | 6/2017 |
| KR | 101770254 B1 | 8/2017 |
| TW | 522226 B | 3/2003 |
| WO | 1999054700 A2 | 10/1999 |
| WO | 02066950 A1 | 8/2002 |
| WO | 2008021311 A2 | 2/2008 |
| WO | 2015073687 A1 | 5/2015 |
| WO | 2016045791 A1 | 3/2016 |
| WO | 2016162673 A1 | 10/2016 |
| WO | 2017069979 A1 | 4/2017 |
| WO | 2018121478 A1 | 7/2018 |
| WO | 2018227153 A1 | 12/2018 |
| WO | 2019246280 A1 | 12/2019 |
| WO | 2020007684 A1 | 1/2020 |
| WO | 2020028353 A1 | 2/2020 |
| WO | 2020086499 A1 | 4/2020 |
| WO | 2020206006 A1 | 10/2020 |
| WO | 2020206020 A1 | 10/2020 |
| WO | 2021055902 A1 | 3/2021 |
| WO | 2021158916 A1 | 8/2021 |
| WO | 2022093864 A1 | 5/2022 |
| WO | 2022211837 A1 | 10/2022 |

OTHER PUBLICATIONS

Kelly J F et al. "A capillary absorption spectrometer for stable carbon isotope ratio (C/C) analysis in very small samples", Review of Scientific Instruments, American Institute of Physics, 2 Huntington Quadrangle, Melville, NY 11747, vol. 83, No. 2, Feb. 1, 2012 (Feb. 1, 2012), pp. 23101-23101, XP012161835, ISSN: 0034-6748, DOI: 10.1063/1.3680593.

Krings et al., Atmos. Meas. Tech., 11, 721-739, Feb. 7, 2018.

International Search Report and Written Opinion for PCT/US2021/016821 mailed Apr. 26, 2021.

"SAFESITE Multi-Threat Detection System", Jul. 11, 2012 (Jul. 11, 2012), pp. 1-6, XP055245980.

International Search Report and Written Opinion for PCT/US21/56710, mailed Feb. 23, 2022.

International Search Report and Written Opinion for PCT/US19/38011 mailed Sep. 9, 2019.

International Search Report and Written Opinion for PCT/US19/38015, mailed Oct. 18, 2019.

International Search Report and Written Opinion for PCT/US19/44119, mailed Oct. 17, 2019.

International Search Report and Written Opinion for PCT/US20/26228 mailed Jul. 1, 2020.

International Search Report and Written Opinion for PCT/US20/26232 mailed Jun. 26, 2020.

International Search Report and Written Opinion for PCT/US20/26246 mailed Jun. 29, 2020.

International Search Report and Written Opinion for PCT/US20/51696, mailed Feb. 3, 2021.

International Search Report and Written Opinion for PCT/US2020/044978, mailed Oct. 26, 2020.

International Search Report and Written Opinion for PCT/US2021/024177, mailed Jun. 23, 2021.

International Search Report and Written Opinion for PCT/US2021/056708, mailed Jan. 27, 2022.

International Search Report and Written Opinion for PCT/US21/42061, mailed Nov. 26, 2021.

International Search Report and Written Opinion for PCT/US21/44532, mailed Jan. 11, 2022.

International Search Report and Written Opinion of PCT/US19/57305, mailed Jan. 2, 2020.

International Search Report and Written Opinion of PCT/US20/54117, mailed Dec. 22, 2020.

Joly, "Atmospheric Measurements by Ultra-Light Spectrometer (AMULSE) Dedicated to Vertical Profile In Situ Measurements of Carbon Dioxide (CO2) Under Weather Balloons: Instrumental Development and Field Application," Sensors 2016, 16, 1609.

Khan, "Low Power Greenhouse Gas Sensors for Unmanned Aerial Vehicles", Remote Snse. 2012, 4, 1355-1368.

Villa. "An Overview of Small Unmanned Aerial Vehicles for Air Quality Measurements: Present Applications and Future Prospectives". Sensors. Web . Jul. 12, 2016.

White, "Development of an Unmanned Aerial Vehicle for the Measurement of Turbulence in the Atmospheric Boundary Layer", Atmosphere, v.8, issue 10, 195, pp. 1-25.

Lilian Joly, The evolution of AMULSE (Atmospheric Measurements by Ultra-Light Spectrometer) and its interest in atmospheric applications. Results of the Atmospheric Profiles of Greenhouse gasEs (APOGEE) weather balloon release campaign for satellite retrieval validation, p. 1-28, Sep. 25, 2019, Atmospheric Measurement Techniques Discussion (Joly).

International Search Report and Written Opinion for PCT/US23/13893, mailed Jun. 30, 2023.

IEEE Conference Paper, "Research of the high pressure jet performance of small size nozzle," ISBN :978-1-5090-1087-5,Publication

(56) References Cited

OTHER PUBLICATIONS

Date : Oct. 1, 2016, Conference dates Oct. 10, 2016 thru Oct. 12, 2016.[retrieved from the Internet] on Sep. 1, 2023 at 4:14pm.
International Search Report and Written Opinion for PCT/US2023/023933 mailed Sep. 26, 2023.
Clilverd, mark A. et al., Energetic particle injection, acceleration, and loss during the geomagnetic disturbances which upset Galaxy 15, Journal of Geophysical Research, vol. 117, A12213, doi: 10.1029/2012JA018175, 2012, pp. 1-16 (Year:2012).
Kem, Christoph et al., Spatial Distribution of Halogen Oxides in the Plume of Mount Pagan Volcano, Mariana Islands, Geophysical Research Letters 10.1029/2018GL079245, Sep. 27, 2018, pp. 9588-9596 (Year:2018).
Liao, J. et al. Observations of Inorganic bromine(HOBr, BrO, and Br2) speciation at Barrow, Alaska in spring 2009, Journal of Geophysical Research, vol. 117, D00R16, doi:10.1029/2011JD016641, 2012, pp. 1-11 (Year:2012).
Liu, Siwen et al., Development of a UAV-Based System to Monitor Air Quality over an Oil Field, Montana Technological University, Montana tech Library Digital Commons @ Montana Tech Graduate Theses & Non-Theses, Fall 2018, pp. 1-85 (Year:2018).
Miyama, Toru et al., Estimating allowable carbon emission for CO2 concentration stabilization using a GCM-based Earth system model, Geophysical Research Letters, vol. 36,L19709, doi:10.1029/2009GL039678, 2009, pp. 0094-8276 (Year:2009).
Oppenheimer Clive et al., Ultraviolet Sensing of Volcanic Sulfur Emissions, Elements (An Internatioknal Magazine of Mineralogy, Geochemistry, and Petrology), Apr. 2010, vol. 6, pp. 87-92 (Year: 2010).
Parazoo, Nicholas C. et al., Interpreting seasonal changes in the carbon balance of southern Amazonia using measurements of XCO2 and chlorophyll fluorescence from GOSAT, Geophysical Research Letters, vol. 40.2829-2833, doi: 10.1002/grl.50452, 2013 pp. 0 2829-2833 (Year:2013).
Queiber, Manuel et al., A new frontier in CO2 flux measurements using a highly portable DIAL laser system, Scientific Reports, DOI: 10.1038/srep33834 1, Sep. 22, 2016, pp. 1-13(Year:2016).
Queiber, Manuel et al., Large-area quantification of subaerial CO2 anomalies with portable laser remote sensing and 2d tomography, the Leading Edge Mar. 2018, pp. 306-313 (Year:2018).
Cabreira et al. "Survey on Coverage Path Planning with Unmanned Aerial Vehicles", published: Drones, published: Jan. 2019, pp. 1-38, year 2019.
Development of a mobile tracer correlation method for assessment of air emissions from landfills and other area sources, Atmospheric Environment 102 (2015) 323-330. T.A. Foster-Wittig et. al. 2015.
Measurements of Methane Emissions from Landfills Using a Time Correlation Tracer Method Based on FTIR Absorption Spectroscopy, Environ. Sci. Technol. 2001, 35, 21-25, B. Galle et. al. 2001.
International Search Report and Written Opinion for PCT/US23/23905 mailed Oct. 5, 2023.
Feng, Lingbing, Nowak, Gen, O'Neill, T.J., Welsh, A.H. "Cutoff; A spatio-temporal imputation method." Journal of Hydrology 519 (2014) : 3591-3605 (Year:2014).
Uehara, K: "Dependence of harmonic signals 1-15 on sample-gas parameters in wavelength-modulation spectroscopy for precise absorption measurements", Applied Physics B, Springer Berlin Heidelberg, Berlin/Heidelberg, vol. 67, Jan. 2, 1998, pp. 517-523, XP007921671, ISSN:0946-2171, DOI: 10.1007/S003400050537.
Field Trial of Methane Emission Quantification Technologies, Society of Petroleum Engineers, SPE-201537-MS, Allen et al., Oct. 2020.
Lilian Joly, The evolution of AMULSE (Atmospheric Measurements by Ultra-Light Spectrometer) and its interest in atmospheric applications. Results of the Atmospheric Pro?les of Greenhouse gasEs (APOGEE) weather balloon release campaign for satellite retrieval validation, p. 1-28, Sep. 25, 2019, Atmospheric Measurement Techniques Discussion (Joly).†

\* cited by examiner
† cited by third party

MULTISPECIES MEASUREMENT PLATFORM USING ABSORPTION SPECTROSCOPY FOR MEASUREMENT OF CO-EMITTED TRACE GASES

CROSS-REFERENCE TO RELATED APPLICATION

This application claims the priority benefit of U.S. Provisional Patent Application Ser. No. 63/170,303 filed Apr. 2, 2021, incorporated herein by reference in its entirety.

FIELD OF ENDEAVOR

The invention relates generally to trace gases, and more particularly to the measurement of multiple trace gas species.

BACKGROUND

Methane ($CH_4$) is an odorless and colorless naturally occurring organic molecule, which is present in the atmosphere at average ambient levels of approximately 1.85 ppm as of 2018 and is projected to continually climb. While methane is found globally in the atmosphere, a significant amount is collected or "produced" through anthropogenic processes including exploration, extraction, and distribution of petroleum in the form of natural gas. Methane is almost always present when other volatile organic compounds (VOCs) are released into the atmosphere, either due to natural or anthropogenic processes. Natural gas, an odorless and colorless gas, is a primary source of energy used to produce electricity and heat. The main component of natural gas is methane. While extraction of natural gas is a large source of methane released to the atmosphere, major contributors of methane also include livestock farming (enteric fermentation), and solid waste and wastewater treatment (anaerobic digestion). Optical cells may be used to detect methane and other trace gases that can be present coincidently.

SUMMARY

A system embodiment may include: one or more optical cavities; one or more light sources configured to emit at least one of: a specified wavelength of light and a band of wavelengths of light into the one or more optical cavities such that the emitted light travels one or more path lengths over one or more distances from the light source, where the one or more light sources may be at least one of: tuned to a first trace gas species, tuned to a second trace gas species, and tuned to a continuous wavelength shifting between the first trace gas species and the second trace gas species; and one or more photovoltaic detectors configured to receive the emitted light that has traveled over the one or more path lengths, where the one or more photovoltaic detectors may be configured to detect at least one of: the first trace gas species and the second trace gas species.

In additional system embodiments, T the one or more optical cavities comprise at least one mirror. In additional system embodiments, the one or more optical cavities comprise at least two mirrors. In additional system embodiments, the one or more light sources comprise at least one of: a laser, a light-emitting diode (LED), a superluminescent diode (SLD), and a lamp. In additional system embodiments, the first trace gas species comprises at least one of: methane and carbon dioxide and the second trace gas species comprises at least one of: methane and carbon dioxide.

In additional system embodiments, the one or more optical cavities comprise two optical cavities. In additional system embodiments, the one or more light sources comprise two light sources. In additional system embodiments, the one or more photovoltaic detectors comprise two photovoltaic detectors.

Another system embodiment may include: an optical cavity; a light source configured to emit a specified band of wavelengths of light into the optical cavity such that the emitted light travels a path length over a distance from the light source, where the light source may be tuned to a continuous wavelength shifting between a first trace gas species and a second trace gas species; and a photovoltaic detector configured to receive the emitted light that has traveled over the path length, where the photovoltaic detector may be configured to detect the first trace gas species and the second trace gas species.

Additional system embodiments may include: one or more mirrors disposed in the optical cavity. In additional system embodiments, the one or more light sources comprise at least one of: a laser, a light-emitting diode (LED), a superluminescent diode (SLD), and a lamp; where the first trace gas species comprises at least one of: methane and carbon dioxide; and where the second trace gas species comprises at least one of: methane and carbon dioxide.

A method embodiment may include: gathering N species concentrations simultaneously downwind of an emissions source using one or more trace gas sensors; using from 1 to N−1 species as an uncontrolled tracer gas to determine an extent of a source plume downwind and cross-validate the concentration species measurements; and attributing emissions to one or more source equipment based on the cross-validated concentration measurements.

Additional method embodiments may include: using at least one of: the N species concentrations, a positional data, and a wind vector to quantify a volumetric flux of the emissions. Additional method embodiments may include: using the N species concentrations, a positional data, and a wind vector to quantify a volumetric flux of the emissions. Additional method embodiments may include: using at least one of: the N species concentrations, a temperature, a pressure, a positional data, and a wind vector to quantify a mass flux. Additional method embodiments may include: using the N species concentrations, a temperature, a pressure, a positional data, and a wind vector to quantify a mass flux.

In additional method embodiments, the uncontrolled tracer gas may be at least one of: carbon dioxide, nitrogen oxides, sulfur oxides, and water vapor, and where the emissions may be methane. Additional method embodiments may include: determining a destruction efficiency of combustion sources based on the N species concentrations. Additional method embodiments may include: determining an efficiency of a methanisation process in a biogas production based on the N species concentrations. Additional method embodiments may include: determining an efficiency of a gas upgrade process in a biogas production based on the N species concentrations.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which.

DETAILED DESCRIPTION

The following description is made for the purpose of illustrating the general principles of the embodiments discloses herein and is not meant to limit the concepts disclosed herein. Further, particular features described herein can be used in combination with other described features in each of the various possible combinations and permutations. Unless otherwise specifically defined herein, all terms are to be given their broadest possible interpretation including meanings implied from the description as well as meanings understood by those skilled in the art and/or as defined in dictionaries, treatises, etc.

The present system allows for a measurement of carbon dioxide ($CO_2$) alongside methane ($CH_4$). The system may use tunable diode laser absorption spectroscopy (TDLAS) to measure co-emitted trace gases, such as carbon dioxide and methane. The system may use a combination of one or two cavities, one or two lasers, and one or two detectors. In some embodiments, the system may use a semi-transparent facet for one of the laser detectors.

The system may measure trace gas concentrations for the two or more gas species downwind of an emissions source. The system may be used to determine the source and concentration of the two or more gas species. While methane and carbon dioxide are shown as the two species, the process and mechanisms described below can be extended to multiple chemical species, depending upon the specific application and environment. For example, there may be cases where methane and ethane could be the species of interest. The disclosed system may use a combination of analog signal processing and/or digital signal processing to determine the species concentration of the two or more gas species. The species concentration may be determined via a signal measurement at the peak wavelength, a look-up table, and/or a non-linear regression and high-resolution transmission molecular absorption (HITRAN) database. In some embodiments, flare models may be used to determine system requirements for co-emitted species. These system requirements may include the dynamic range for the trace gases to be measured. Other modeling types are possible and contemplated.

A laser and laser detector are described as being representative. In some embodiments, the laser may be a light source, such as a light-emitting diode (LED), a superluminescent diode (SLD), a lamp, and the like. In some embodiments, the laser detector may be a light detector, such as a photovoltaic detector.

Methane and carbon dioxide are described as being representative of a first trace gas species and a second trace gas species. In some embodiments, any two trace gases or species may be used in the system and method disclosed herein. The system and method disclosed herein for the detection and subsequent quantification of more than two species can be extended in a manner similar to that used to extend the process from one to two species.

Figure 1A:
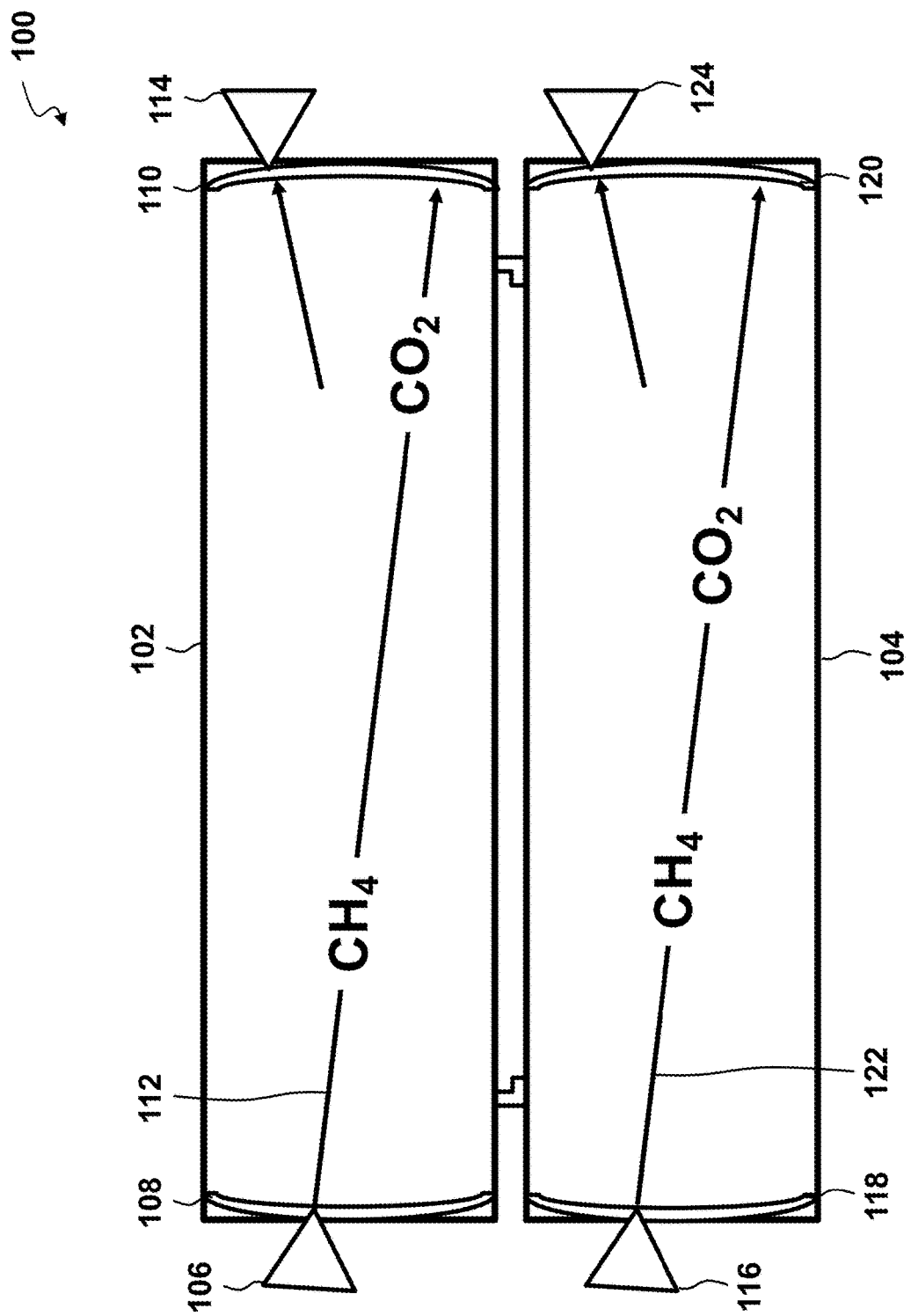
FIG. 1A depicts a cross-sectional view of a system having two cavities for separate carbon dioxide and methane measurements on a same conveyance platform, according to one embodiment.

FIG. 1A depicts a cross-sectional view of a system having two cavities for separate carbon dioxide and methane measurements on a same conveyance platform, according to one embodiment. The system 100 includes two cavities 102, 104 for separate carbon dioxide and methane measurements on a same conveyance platform.

The first cavity 102 includes a first tuned laser source for methane ($CH_4$) 106. The first cavity 102 includes two mirrors 108, 110 so that the light from the first tuned laser 106 can travel a path length 112 having multiple reflections across the two mirrors 108, 110 in the open first cavity 102. The laser path length 112 terminates at a first laser detector 114 configured to detect a concentration of methane.

The second cavity 104 includes a second tuned laser source for carbon dioxide ($CO_2$) 116. The second cavity 104 includes two mirrors 118, 120 so that the light from the second tuned laser 116 can travel a path length 122 having multiple reflections across the two mirrors 118, 120 in the open second cavity 104. The laser path length 122 terminates at a second laser detector 124 configured to detect a concentration of carbon dioxide.

Figure 1B:
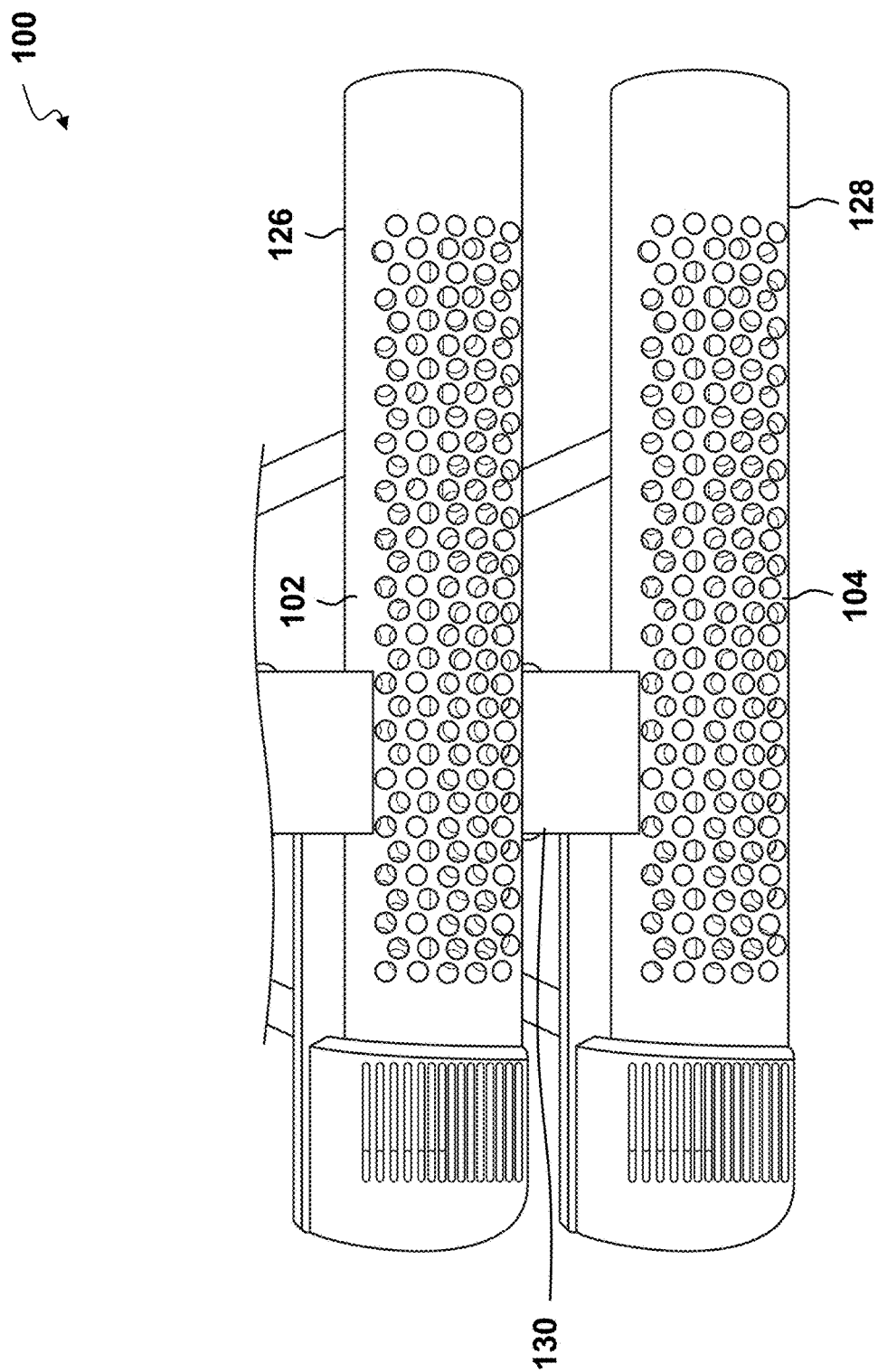
FIG. 1B depicts a perspective view of the system of FIG. 1A, according to one embodiment.

FIG. 1B depicts a perspective view of the system 100 of FIG. 1A, according to one embodiment. Each cavity 102, 104 may have a protective cover 126, 128 so as to protect the optical cells from damage, dust, or the like. Each cavity 102, 104 may be disposed proximate to one another so that the measurements of carbon dioxide and methane are co-located. In some embodiments, a connector 130 may connect the cavities 102, 104 together in close proximity. In some embodiments, the connector 130 may connect the protective covers 126, 128 of each cavity 102, 104.

Figure 2:
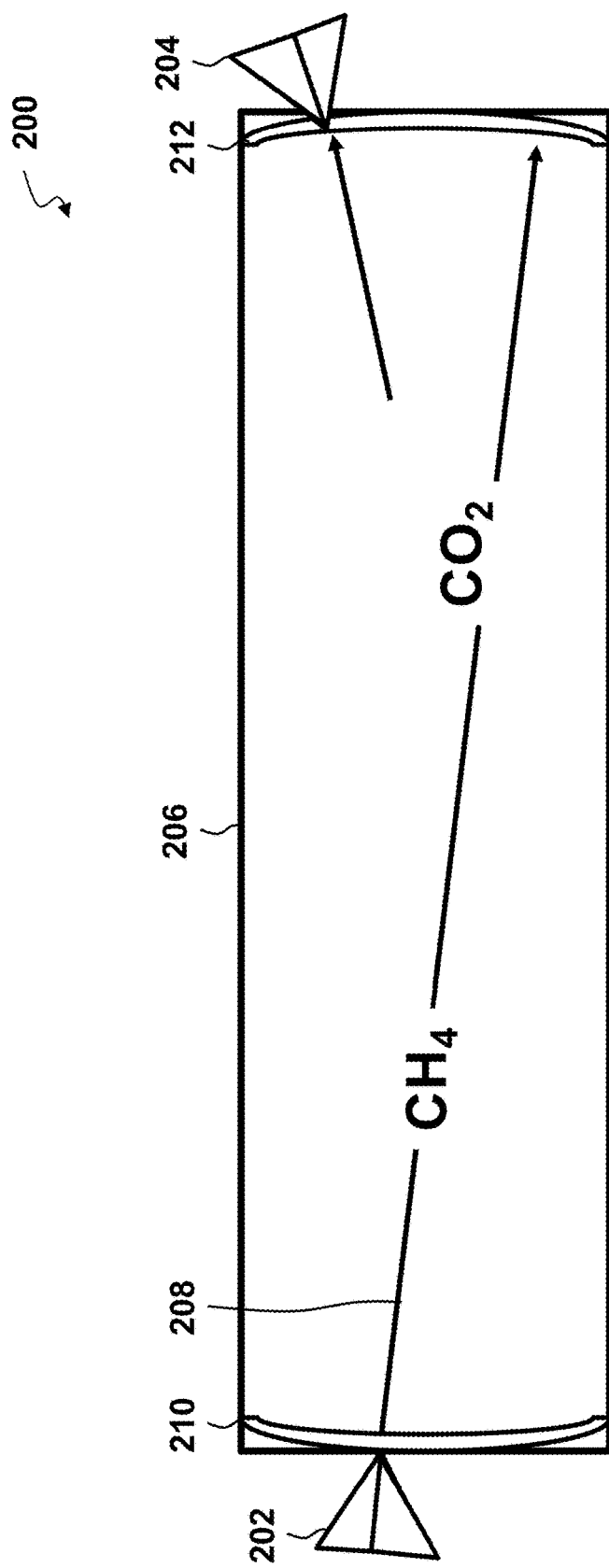
FIG. 2 depicts a cross-sectional view of a system having one laser and one detector in one cavity with the frequency adjusted to the absorption frequencies of carbon dioxide and methane, according to one embodiment.

FIG. 2 depicts a cross-sectional view of a system 200 having one laser 202 and one detector 204 in one cavity 206 with the frequency of the laser 202 and detector 204 adjusted to the absorption frequencies of carbon dioxide and methane, according to one embodiment. The system includes a single laser source 202 with a continuous wavelength shifting between carbon dioxide and methane. The single laser source 202 may be a dual wavelength tuned laser source. The system 200 includes a single laser 202 and detector 204 that can be used to detect both carbon dioxide and methane based on the continuous wavelength of the laser 202 shifting between carbon dioxide and methane. The laser 202 can travel a path length 208 having multiple reflections across the two mirrors 210, 212 in the open cavity 206. The laser path length 208 terminates at the laser detector 204 configured to detect a concentration of carbon dioxide and methane.

Figure 3:
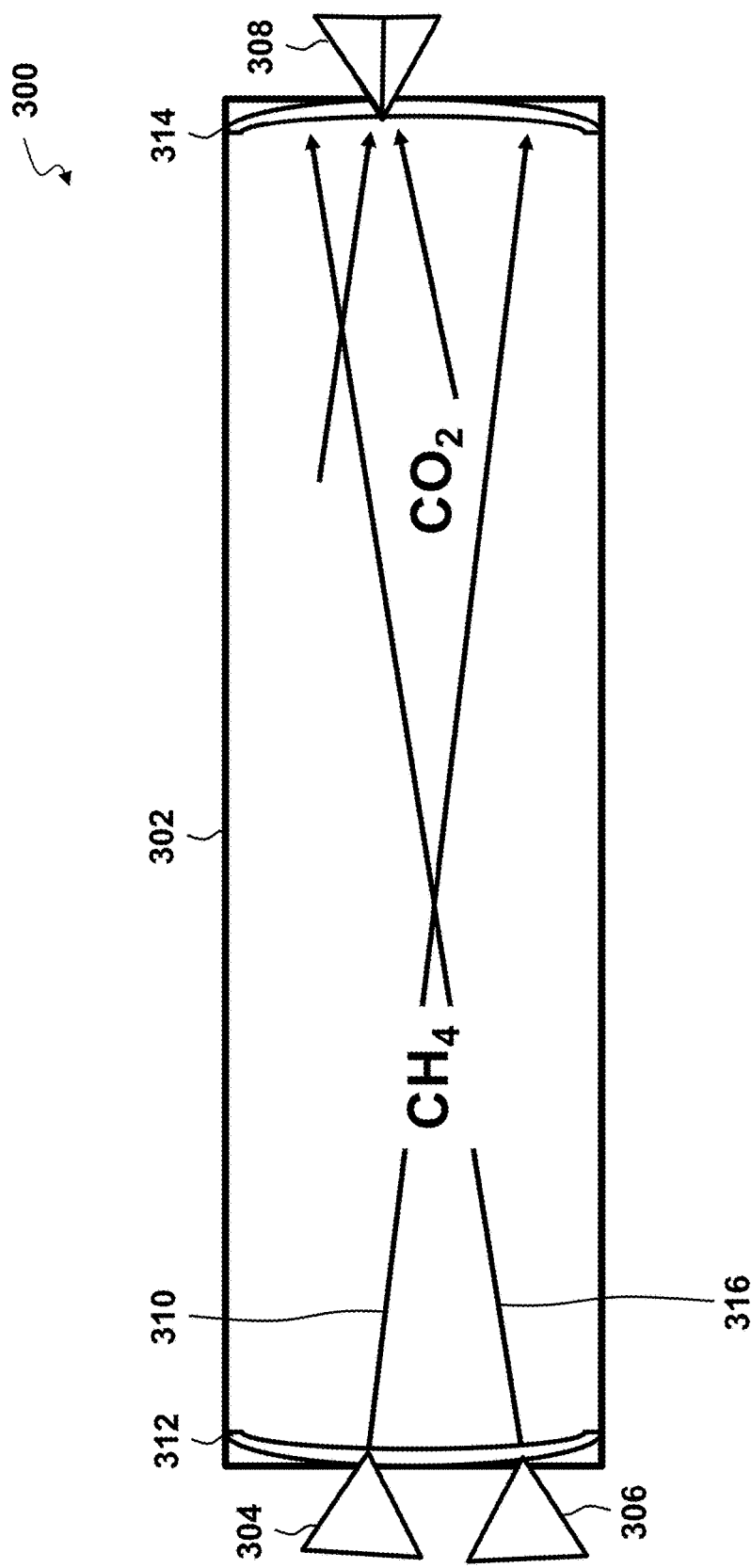
FIG. 3 depicts a cross-sectional view of a system having one cavity with two lasers and one detector, according to one embodiment.

FIG. 3 depicts a cross-sectional view of a system 300 having one cavity 302 with two lasers 304, 306 and one detector 308, according to one embodiment. A first laser source 304 may be turned for methane. The first laser 304 can travel a first path length 310 having multiple reflections across the two mirrors 312, 314 in the open cavity 302. The first path length 310 terminates at the laser detector 308 configured to detect a concentration of carbon dioxide and methane. A second laser source 306 may be tuned for carbon dioxide. The second laser 306 can travel a second path length 316 having multiple reflections across the two mirrors 312, 314 in the open cavity 302. The second path length 316 terminates at the laser detector 308 configured to detect a concentration of carbon dioxide and methane. The single laser detector 308 may detect both methane and carbon dioxide.

Figure 4:
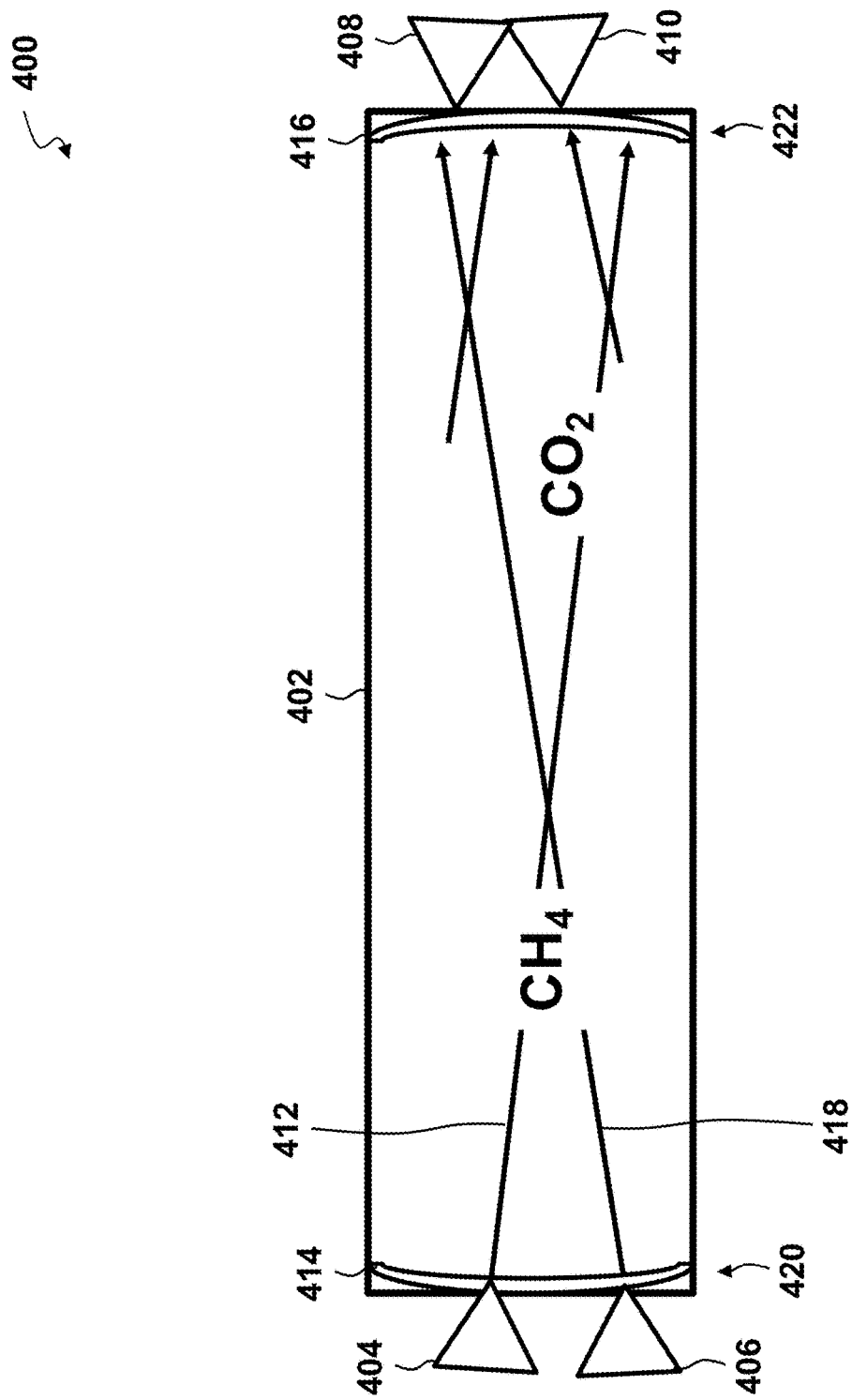
FIG. 4 depicts a cross-sectional view of a system having one cavity with two lasers and two detectors, where the detectors are on the same side, according to one embodiment.

FIG. 4 depicts a cross-sectional view of a system 400 having one cavity 402 with two laser sources 404, 406 and two detectors 408, 410, where the detectors 408, 410 are on a same side of the cavity 402, according to one embodiment. A first laser source 404 may be turned for methane. The first laser source 404 can travel a first path length 412 having multiple reflections across the two mirrors 414, 416 in the open cavity 402. A second laser source 406 may be tuned for carbon dioxide. The second laser source 406 can travel a second path length 418 having multiple reflections across the two mirrors 414, 416 in the open cavity 402. Both the first laser source 404 and the second laser source 406 may be disposed on a same first side 420 of the cavity 402. A first laser detector 408 may be used to receive the laser light from the first laser and detect a methane concentration. A second laser detector 410 may be used to receive the laser light from the second laser and detect a carbon dioxide concentration. The first laser detector 408 and the second laser detector 410 may be located on a same second side 422 of the cavity 402. The first side 420 of the cavity 402 may be opposite the second side 422 of the cavity 402.

Figure 5:
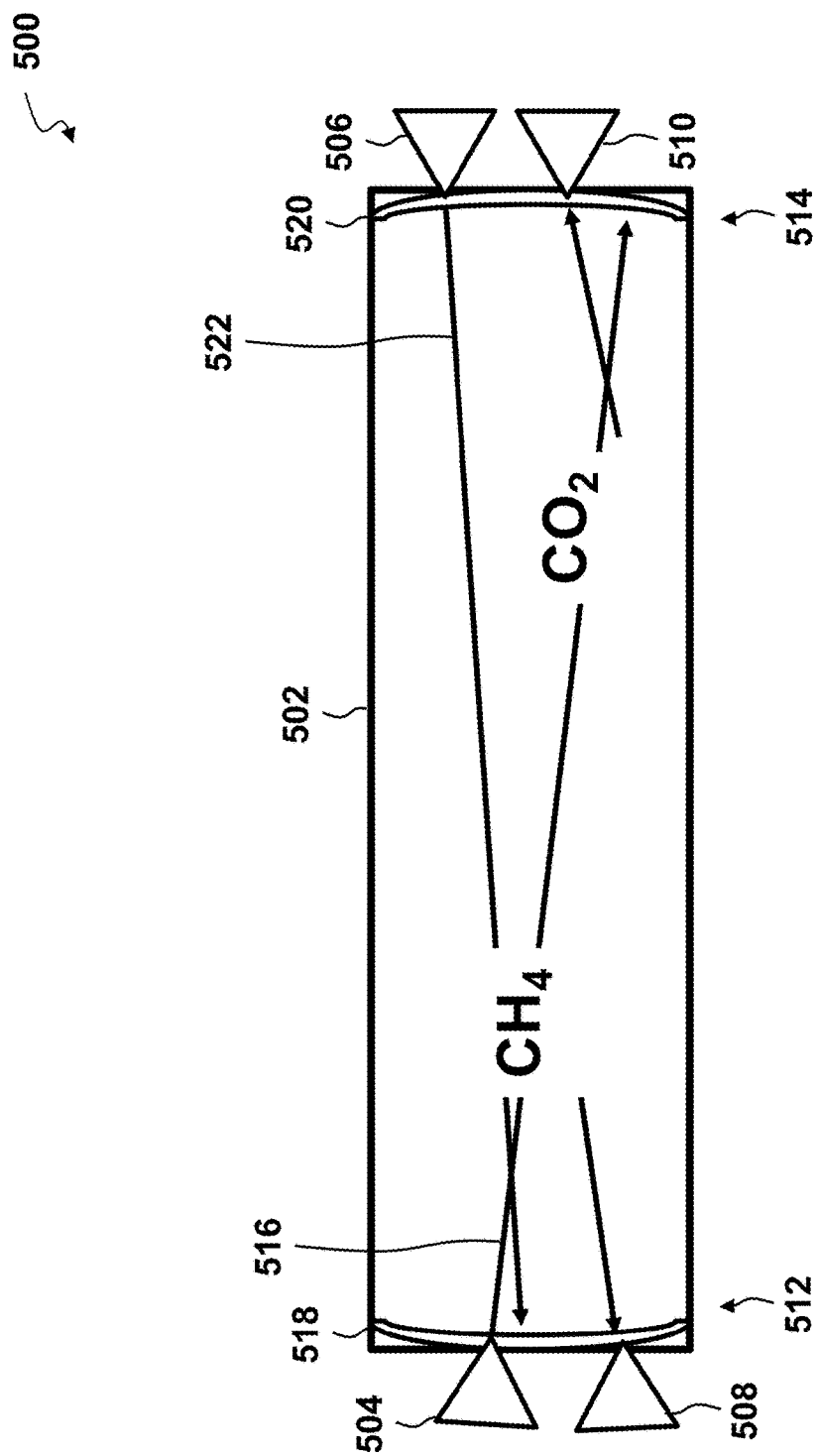
FIG. 5 depicts a cross-sectional view of a system having one cavity with two lasers and two detectors, where the detectors are on opposite sides, according to one embodiment.

FIG. 5 depicts a cross-sectional view of a system 500 having one cavity 502 with two laser sources 504, 506 and two detectors 508, 510, where the detectors 508, 510 are on opposite sides 512, 514 of the cavity 502, according to one embodiment. A first laser source 504 may be turned for methane and may be disposed on a first side 512 of the cavity. A second laser source 506 may be tuned for carbon dioxide and may be disposed on a second side 514 of the cavity 502. The first side 512 of the cavity 502 may be opposite the second side 514 of the cavity 502. A first laser detector 510 may be used to receive the laser light from the first laser 504 and detect a methane concentration. The first laser detector 510 may be located on the second side 514 of the cavity 502 proximate the second laser source 506. A second laser detector 508 may be used to receive the laser light from the second laser source 506 and detect a carbon dioxide concentration. The second laser detector 508 may be located on the first side 512 of the cavity 502 proximate the first laser source 504. The first laser source 504 can travel a first path length 516 having multiple reflections across the two mirrors 518, 520 in the open cavity 502. The second laser source 506 can travel a second path length 522 having multiple reflections across the two mirrors 518, 520 in the open cavity 502.

Figure 6:
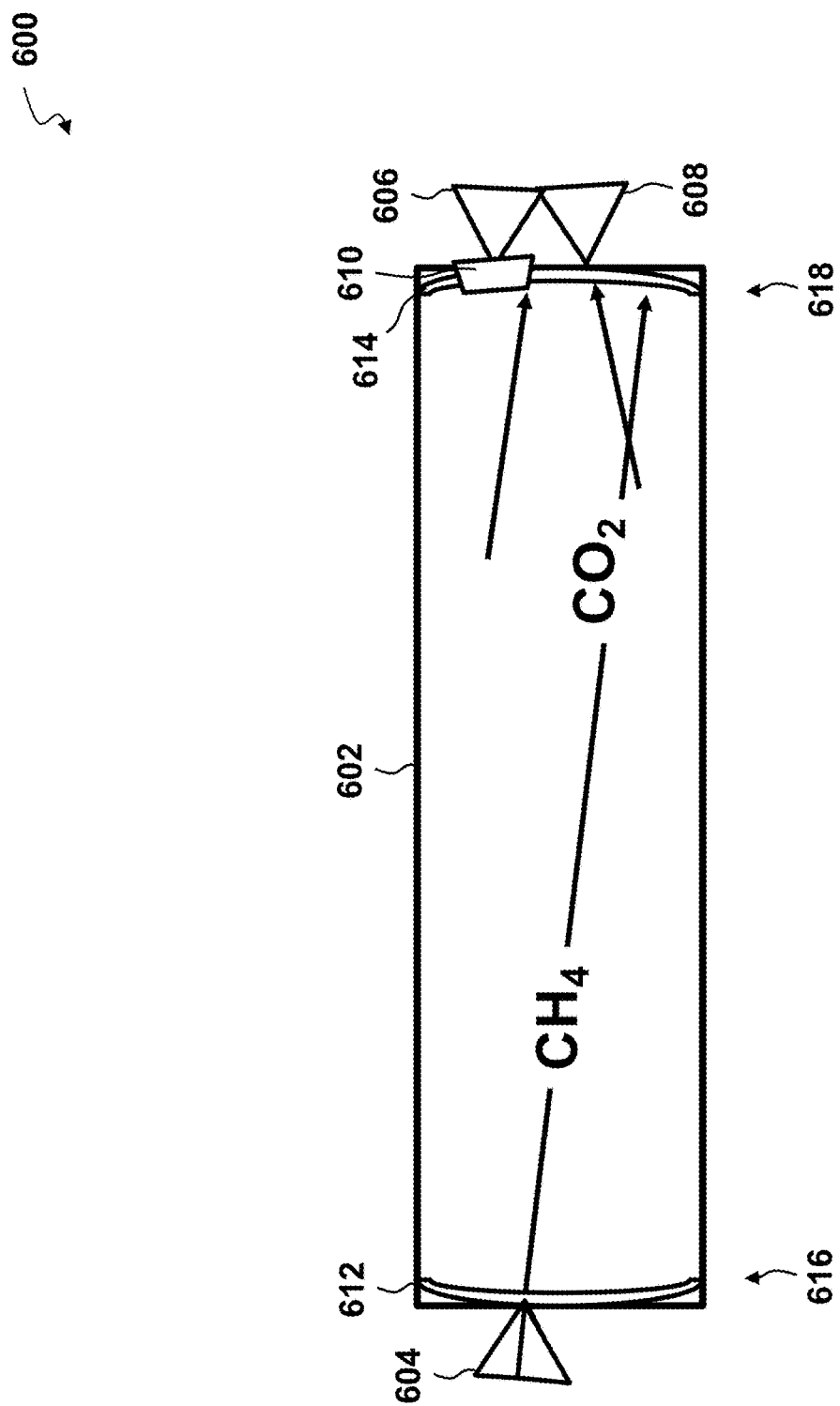
FIG. 6 depicts a cross-sectional view of a system having one cavity with one laser and two detectors with one of the two detectors located behind a semi-transparent facet, according to one embodiment.

FIG. 6 depicts a cross-sectional view of a system 600 having one cavity 602 with one tunable laser source 604 and two detectors 606, 608 with one detector 606 of the two detectors 606, 608 located behind a semi-transparent facet 610, according to one embodiment. For some embodiments, the semi-transparent facet 610 may be a semi-transparent area, a portion of the mirror 614 that allows some light to pass through, an opening in the mirror 614, or the like. A tunable laser source 604 may be located on a first side 616 of the cavity 602. A first laser detector 606 may be located on a second side 618 of the cavity 602. The first side 616 of the cavity 602 may be opposite the second side 618 of the cavity 602. The first laser detector 606 may be configured to detect methane. A second laser detector 608 may be located on the second side 618 of the cavity proximate the first laser detector 606. The first laser detector 606 may be located behind a semi-transparent facet 614 in a mirror 614 of two or more mirrors 612, 614 of the cavity 602. The semi-transparent facet 614 may reduce reflectivity from the remainder of the cavity 602, determined as a function of the laser 604 power and detector 606, 608 responsivity.

In this system 600, one of the laser detectors 606 may be located behind a semi-transparent facet 610. A shorter pathlength may be utilized for the higher absorbing species, and the longer pathlength may be utilized for the lower absorbing species. This system 600 enables sufficient sensitivity for both species using only one tunable laser source 604.

With reference to FIGS. 1A-6, light sources may be discrete with discrete/independent entrance to the respective optical cells. Respective light sources may be discrete with optical or fiber coupling and a single entrance to the respective optical cells. There may be N number of laser sources, where N is a number equal to or greater than one. The wavelength of light sources may be determined by desired absorption characteristics of the gas species of interest. A light source may be coherent, e.g., lasers that are Fabry-Perot (FP), IC distributed feedback laser (DFB), or quantum cascade lasers (QCL). Another light source may be incoherent, e.g., light-emitting diodes (LEDs), superluminescent diodes (SLDs), or lamps. Optical cavities may be an open cavity, an open path, or a closed cavity. In an open cavity, a light source, detector, and optics are in the same assembly with the beam path open to the ambient air. In an open path, a light source is dislocated from the detector. Some embodiments may use pitch and catch (no reflections), retroreflectors, or multi-pass. In a closed cavity, a light source, detector, and optics are in the same assembly with the beam path closed to the ambient air. The sample to be tested for the presence of one or more trace gases may be drawn in by a pump, fan, or other methods that convey gas samples into the chamber. In some embodiments, a lightweight and low power system may include one laser, one detector, and the wavelength shifting may be handled by software. This version will be the lightest and lowest power version. In some embodiments, a dual cavity system may be the easiest to build, but have a higher weight and increased power requirements as compared to the other embodiments disclosed herein.

Figure 7:
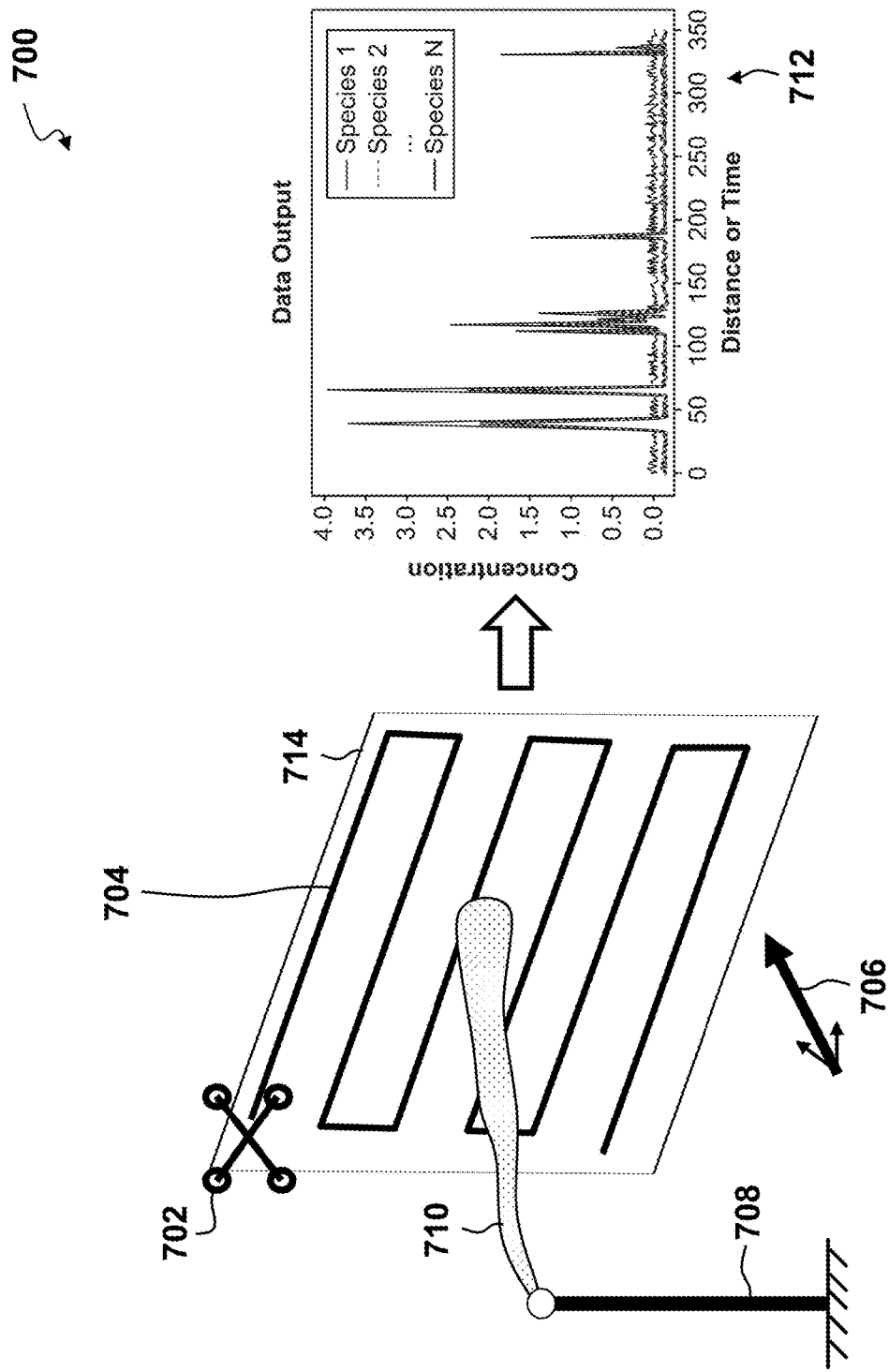
FIG. 7 depicts a system for detecting two or more species of gas using a quantification flight path, according to one embodiment.

FIG. 7 depicts a system 700 for detecting two or more species of trace gases 710 using a quantification flight path, according to one embodiment. The trace gas sensor may be attached to an aerial vehicle 702, such as an unmanned aerial vehicle (UAV), and flown in a raster pattern 704 downwind 706 of one or more gas sources 708 or potential gas sources. The trace gas sensor may detect a concentration of two or more species of trace gases 710 over a measured distance of time. This measured gas concentration 712, when used in conjunction with the wind speed and wind variance, may be used to determine the source 708 of the trace gases 710. FIG. 7 depicts a downwind raster mass-balance quantification approach. In some embodiments, the flight path 704 may form a closed surface flux plane 714 about the trace gas source 708, such that the disclosed system and method utilizes a closed surface quantification approach. The measured concentration 712 shows the concentration on the Y-axis and the distance or time on the X-axis for each measured species of gas from Species 1 to Species N.

Figure 8:
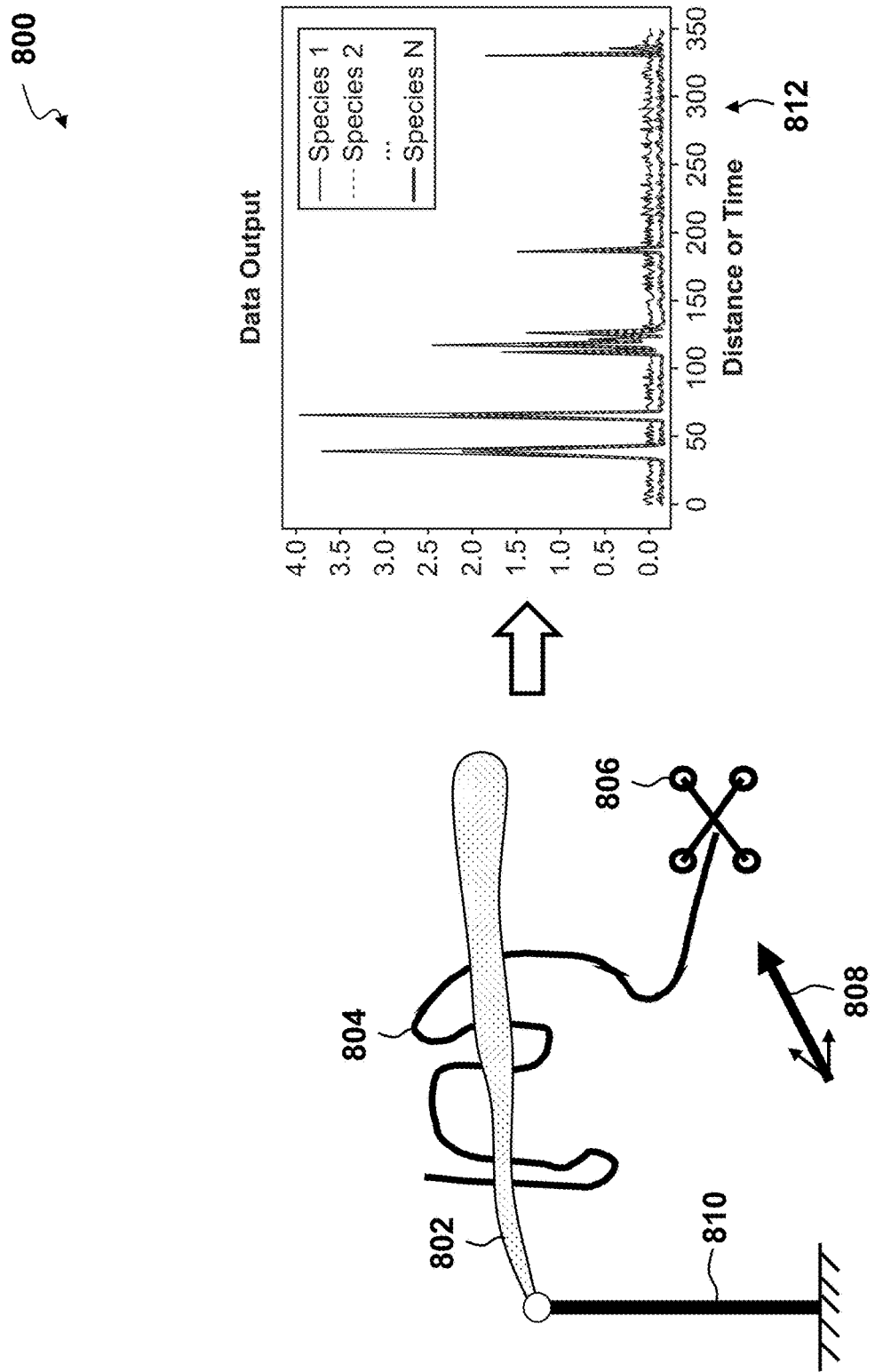
FIG. 8 depicts a system for detecting two or more species of gas using a deflection flight path, according to one embodiment.

FIG. 8 depicts a system for detecting two or more species of trace gases 802 using a deflection flight path 804, according to one embodiment. The trace gas sensor may be attached to an aerial vehicle 806, such as an unmanned aerial vehicle (UAV), and flown in a random or semi-random pattern downwind 808 of a gas source 810 or potential gas source. The trace gas sensor may detect a concentration of two or more species of trace gases 802 over a measured distance of time. This measured gas concentration, when used in conjunction with the wind speed and wind variance 808, may be used to determine the source 810 of the trace gases 802. In some embodiments, the flight path may be a quantification flight path if using an inverse gaussian method of quantification. The measured concentration 812 shows the concentration on the Y-axis and the distance or time on the X-axis for each measured species of gas from Species 1 to Species N.

FIGS. 9A-9D depict high-level flowcharts of method embodiments 900, 901, 903, 905 for multi-species measurements for uncontrolled tracer gas verification, according to one embodiment.

Figure 9A:
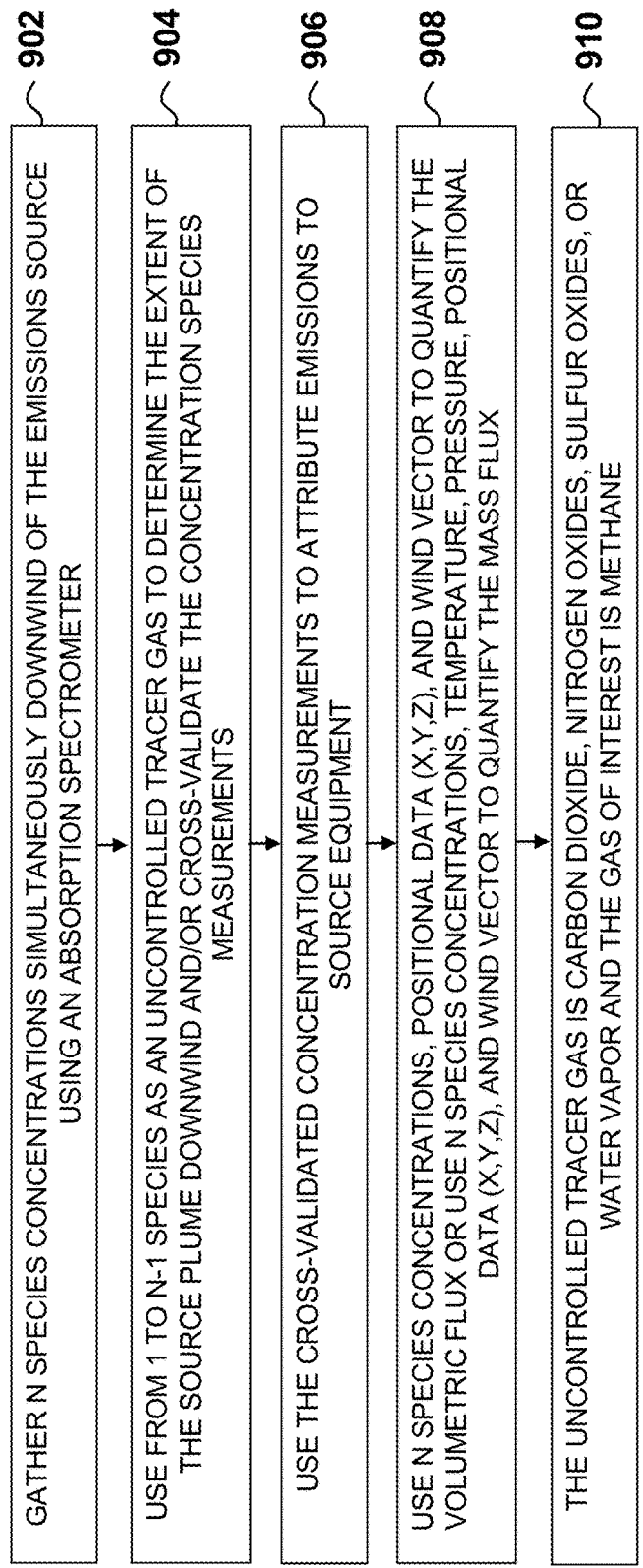
FIGS. 9A-9D depict high-level flowcharts of method embodiments for multi-species measurements for uncontrolled tracer gas verification, according to one embodiment.

In FIG. 9A, the method 900 may include gathering N species concentrations simultaneously downwind of the emissions source using an absorption spectrometer, such as a TDLAS sensor(s) (step 902). The number of species N may be equal to or greater than one. In one embodiment, N species may be two species of trace gases such as carbon dioxide and methane. The method 900 may then include using from 1 to N−1 species that are co-emitted from the emission source as an uncontrolled tracer gas to determine the extent of the source plume downwind and/or cross-validate the concentration species measurements (step 904). This step 904 can happen manually with a human-in-the-loop or autonomously by an unmanned vehicle through dynamic re-tasking. This step 904 may include using the measurements of the concentration distribution of one of the species as a proxy for the distribution of the other species. The method 900 may then include using the cross-validated concentration measurements to attribute emissions to source equipment, given apriori knowledge of the system inspected (e.g. emitting species) (step 906). Optionally, the method 900 may include using N species concentrations, positional data (x,y,z), and a wind vector to quantify the volumetric flux or use N species concentrations, temperature, pressure, positional data (x,y,z), and wind vector to quantify the mass flux (step 908). Optionally, for method 900, the uncontrolled tracer gas may be carbon dioxide, nitrogen oxides, sulfur oxides, or water vapor, and the gas of interest may be methane (step 910).

Figure 9B:
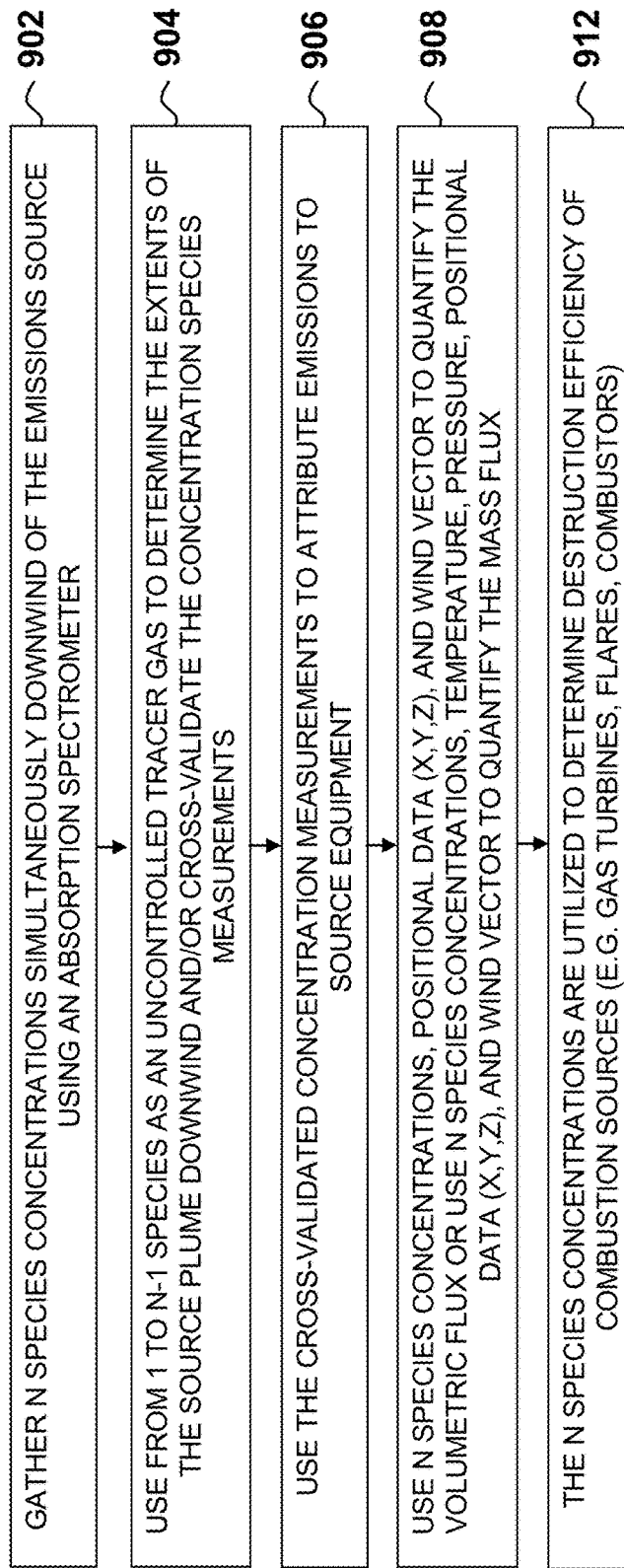

In FIG. 9B, the method 901 may include gathering N species concentrations simultaneously downwind of the emissions source using an absorption spectrometer (step 902). The method 901 may then include using from 1 to N−1 species as an uncontrolled tracer gas to determine the extents of the source plume downwind and/or cross-validate the concentration species measurements (step 904). The method 901 may then include using the cross-validated concentration measurements to attribute emissions to source equipment (step 906). Optionally, the method 901 may include using N species concentrations, positional data (x,y,z), and wind vector to quantify the volumetric flux or use N species concentrations, temperature, pressure, positional data (x,y, z), and wind vector to quantify the mass flux (step 908). Optionally, for the method 901, the N species concentrations may be utilized to determine the destruction efficiency of combustion sources (e.g., gas turbines, flares, combustors) (step 912). The destruction efficiency may be calculated for an item such as a flare, gas turbine, or the like, based on the assumed efficiency of the engine of fuel use. By measuring $CO_2$ and $CH_4$, the disclosed method can actually measure the destruction efficiency rather than use an assumed calculation, and thus make a more informed decision about equipment performance.

Figure 9C:
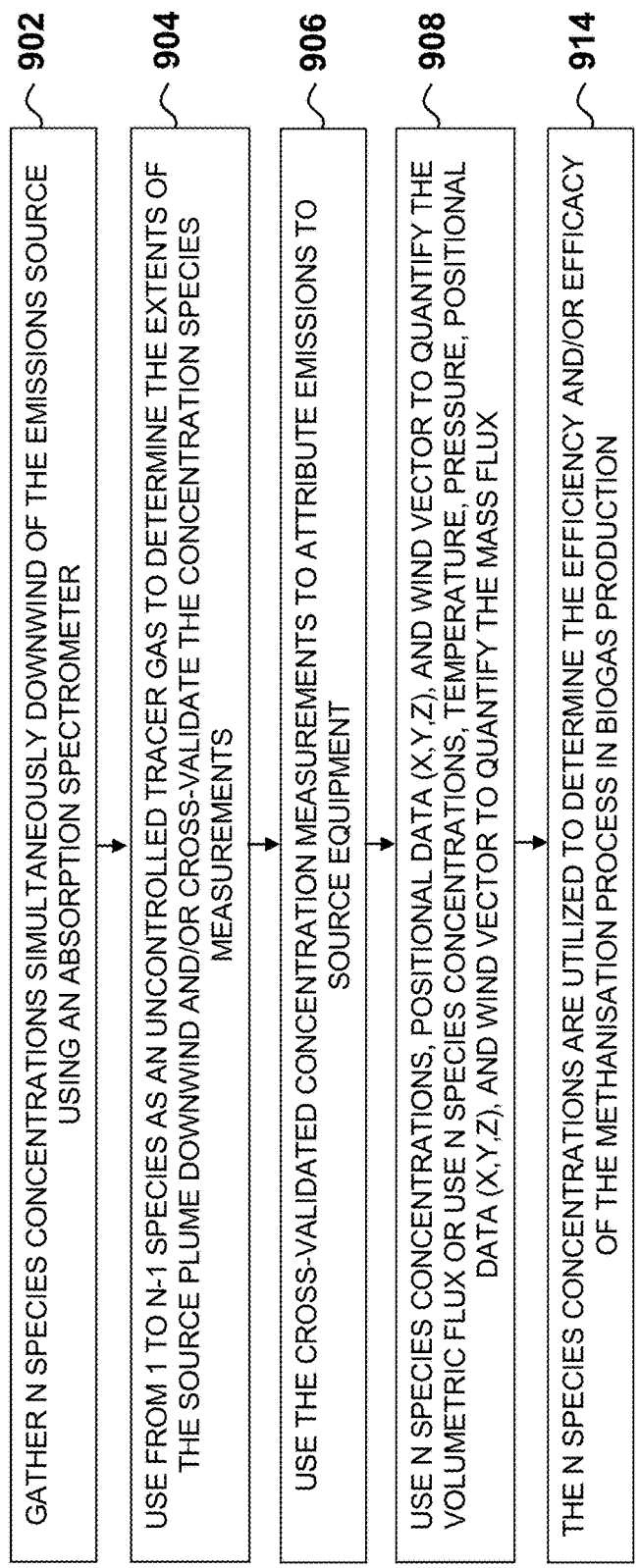

In FIG. 9C, the method 903 may include gathering N species concentrations simultaneously downwind of the emissions source using an absorption spectrometer (step 902). The method 903 may then include using from 1 to N−1 species as an uncontrolled tracer gas to determine the extents of the source plume downwind and/or cross-validate the concentration species measurements (step 904). The method 903 may then include using the cross-validated concentration measurements to attribute emissions to source equipment (step 906). Optionally, the method 903 may include using N species concentrations, positional data (x,y,z), and wind vector to quantify the volumetric flux or use N species concentrations, temperature, pressure, positional data (x,y,z), and wind vector to quantify the mass flux (step 908). Optionally, for the method 903, the N species concentrations may be utilized to determine the efficiency and/or efficacy of the methanisation process in biogas production (step 914). Biogas facilities may perform upgrading of biogas to supply quality natural gas that can be put directly into a pipeline. In a manner akin to that for looking at destruction efficiency of flares, the disclosed method can also ascertain from the multiple species how efficiently this is upgrading is performed. Additionally, the disclosed method can also look at the methane production of any processed digestate that has been through the biogas production/methanogenesis process, and if there is still methane indicated from the sensor survey/measurement then the disclosed method can highlight the inefficiencies in the process.

Figure 9D:
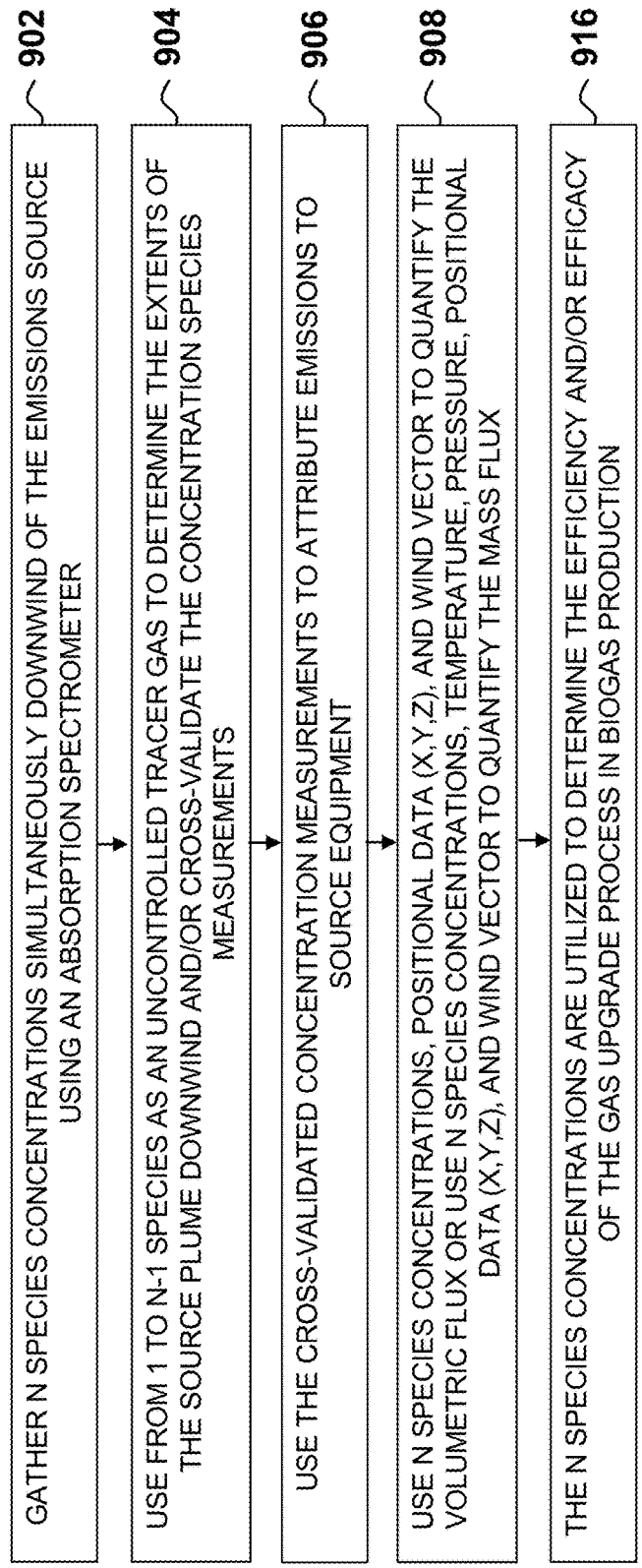

In FIG. 9D, the method 905 may include gathering N species concentrations simultaneously downwind of the emissions source using an absorption spectrometer (step 902). The method 905 may then include using from 1 to N−1 species as an uncontrolled tracer gas to determine the extents of the source plume downwind and/or cross-validate the concentration species measurements (step 904). The method 905 may then include using the cross-validated concentration measurements to attribute emissions to source equipment (step 906). Optionally, the method 905 may include using N species concentrations, positional data (x,y,z), and wind vector to quantify the volumetric flux or use N species concentrations, temperature, pressure, positional data (x,y,z), and wind vector to quantify the mass flux (step 908). Optionally, for the method 905, the N species concentrations may be utilized to determine the efficiency and/or efficacy of the gas upgrade process in biogas production (step 916). This has significant monetary implications for biogas production operators and is useful information for improving the biodigestion operation. As discussed above, biogas production involves organic waste being processed (typically with an anaerobic digestor. By surveying the processed solids and liquids, which may be held in open ponds, the disclosed method may see that there is still methane being emitted, even though the bulk of the biogas has been harvested off. This inefficiency of having 'left over' methane has a cost implication to the biogas producer as the biogas producer may be claiming carbon credits for the produced biogas. These carbon credits can be worth up to 10× the value of the actual gas.

FIGS. 10A-10D depict functional block diagrams of systems 1000, 1001, 1003, 1005 that determine a concentration of two or more species of gas, according to several embodiments. An output from a signal waveform generator 1002 and an output from a modulation waveform generator 1004 may be summed 1005 and input to a laser driver 1006. An output from the laser driver 1006 and a thermoelectric cooler (TEC) driver 1008 may be received by a laser diode 1010. The laser diode 1010 may output a light source 1011 having a desired wavelength. A photodiode 1012 may receive the output light source 1011 to determine a presence of one or more trace gas concentrations passing through the output light source 1011.

Figure 10A:
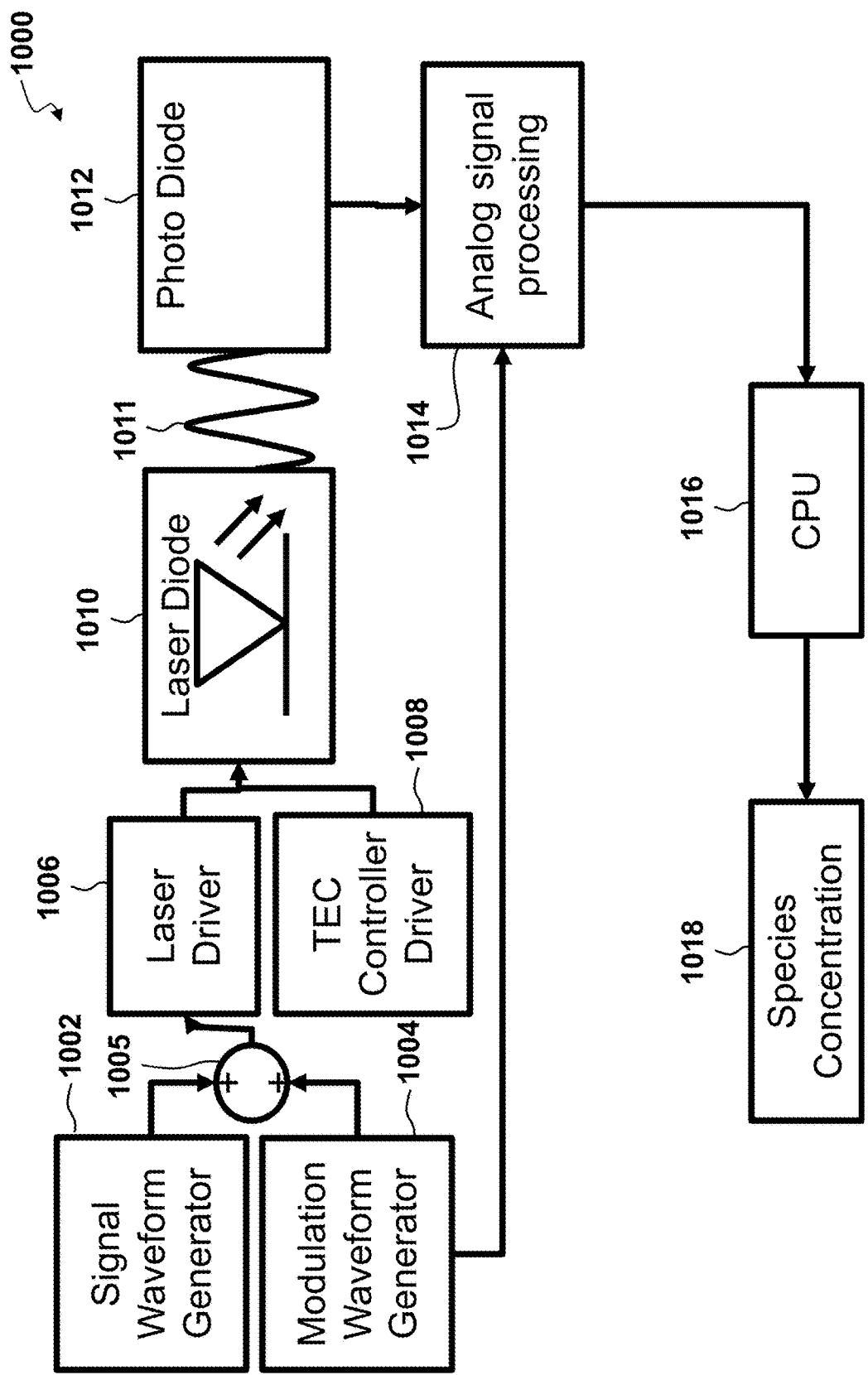
FIGS. 10A-10D depict functional block diagrams of systems that determine a concentration of two or more species of gas, according to several embodiments.

In FIG. 10A, the system 1000 includes an output from the photodiode 1012 that undergoes analog signal processing 1014. The analog signal processor 1014 also receives the output from the modulation waveform generator 1004. The output of the analog signal processing is processed by a central processing unit (CPU) 1016 or other processor and the species concentration 1018 is determined. By using analog signal processing 1014, the conversion to digital by the CPU 1016 may be delayed and less processing power may be required. The system 1000 in FIG. 10A may be the preferred embodiment as compared to the systems in FIGS. 10B-10D as this system 1000 may process data faster and draw less power as compared to the systems in FIGS. 10B-10D.

Figure 10B:
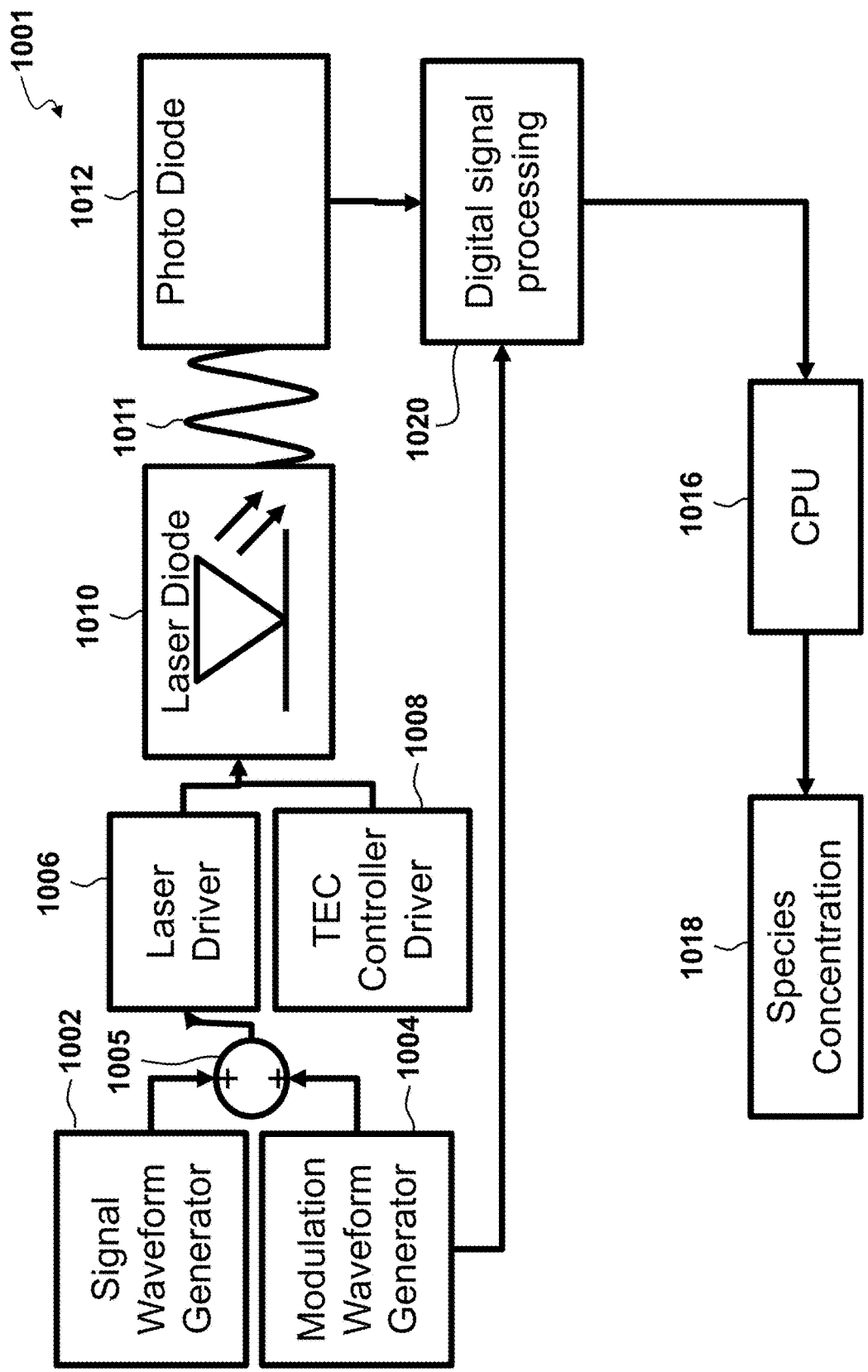

In FIG. 10B, the system 1001 includes the output from the photodiode 1012 that undergoes digital signal processing 1020. The digital signal processor 1020 also receives the output from the modulation waveform generator 1004. The output of the digital signal processing 1020 is processed by a central processing unit (CPU) 1016 or other processor, and the species concentration 1018 is determined.

Figure 10C:
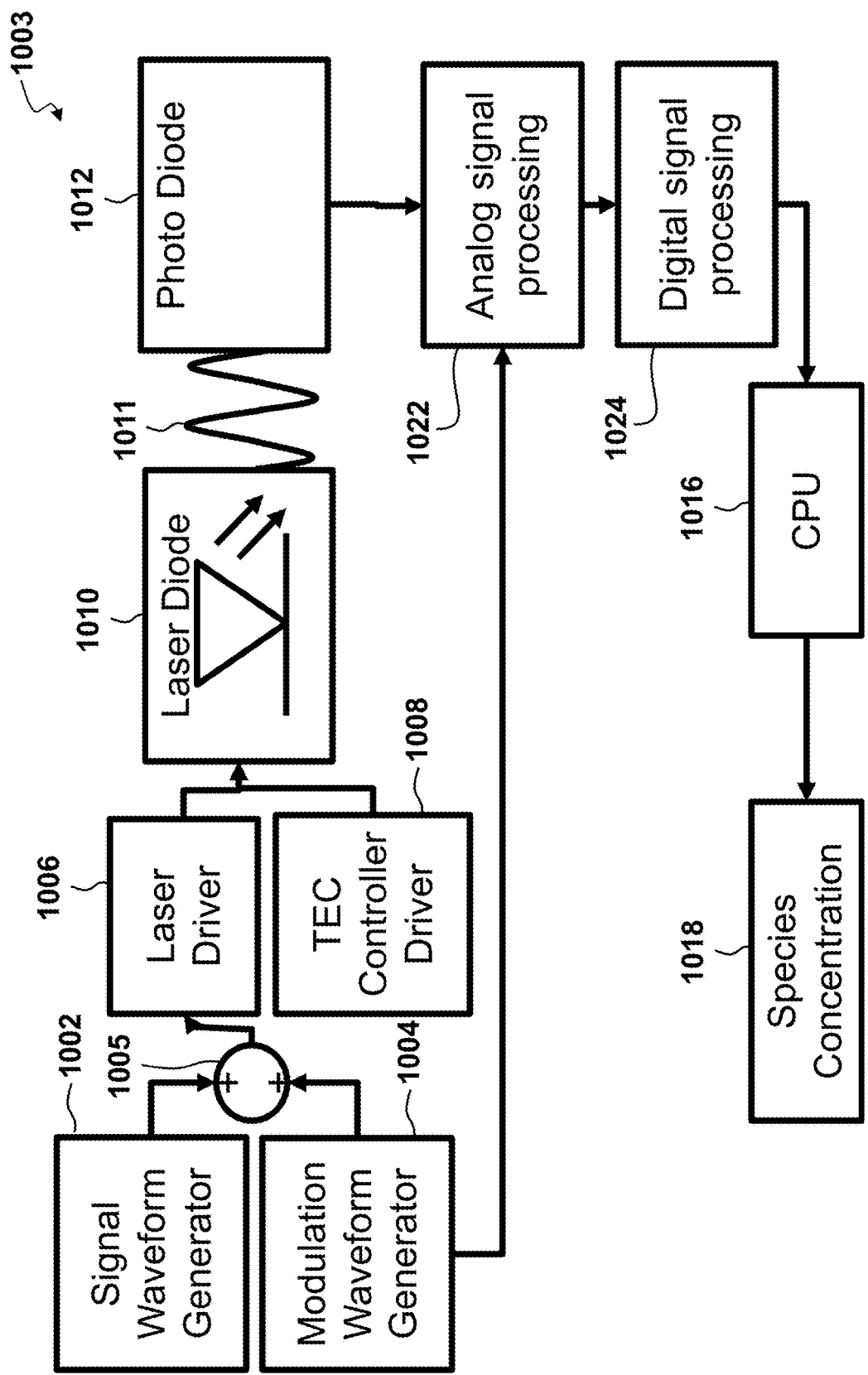

In FIG. 10C, the system 1003 includes the output from the photodiode 1012 that undergoes analog signal processing 1022. The analog signal processor 1022 also receives the output from the modulation waveform generator 1004. The output of the analog signal processing 1022 is processed by digital signal processing 1024 and then processed by a central processing unit (CPU) 1016 or other processor, and the species concentration 1018 is determined.

Figure 10D:
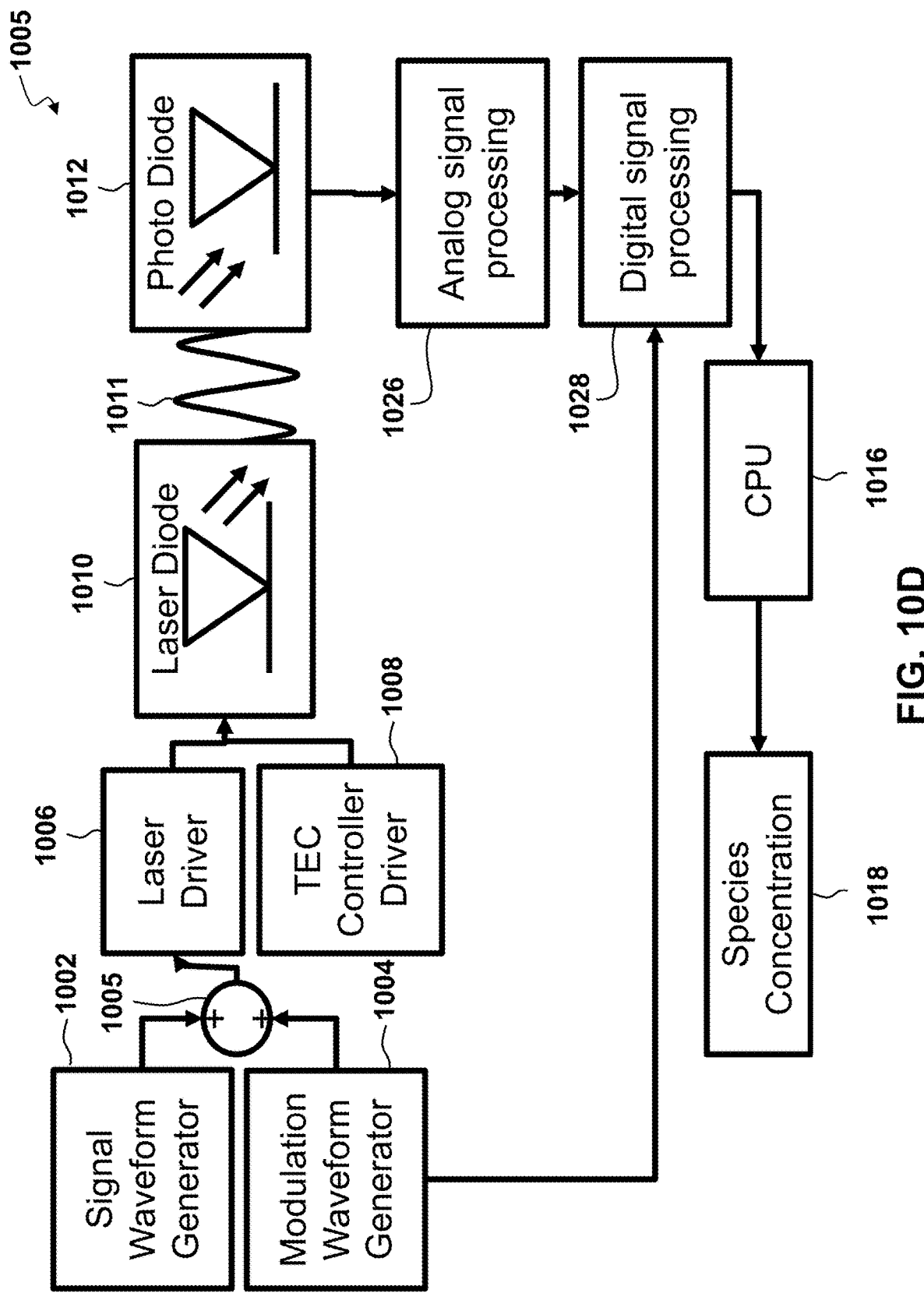

In FIG. 10D, the system 1005 includes the output from the photodiode 1012 that undergoes analog signal processing 1026. The output of the analog signal processing 1026 is processed by digital signal processing 1028. The digital signal processing 1028 also receives the output from the modulation waveform generator 1004. The output from the digital signal processing 1028 is then processed by a central processing unit (CPU) 1016 or other processor and the species concentration 1018 is determined.

Figure 11:
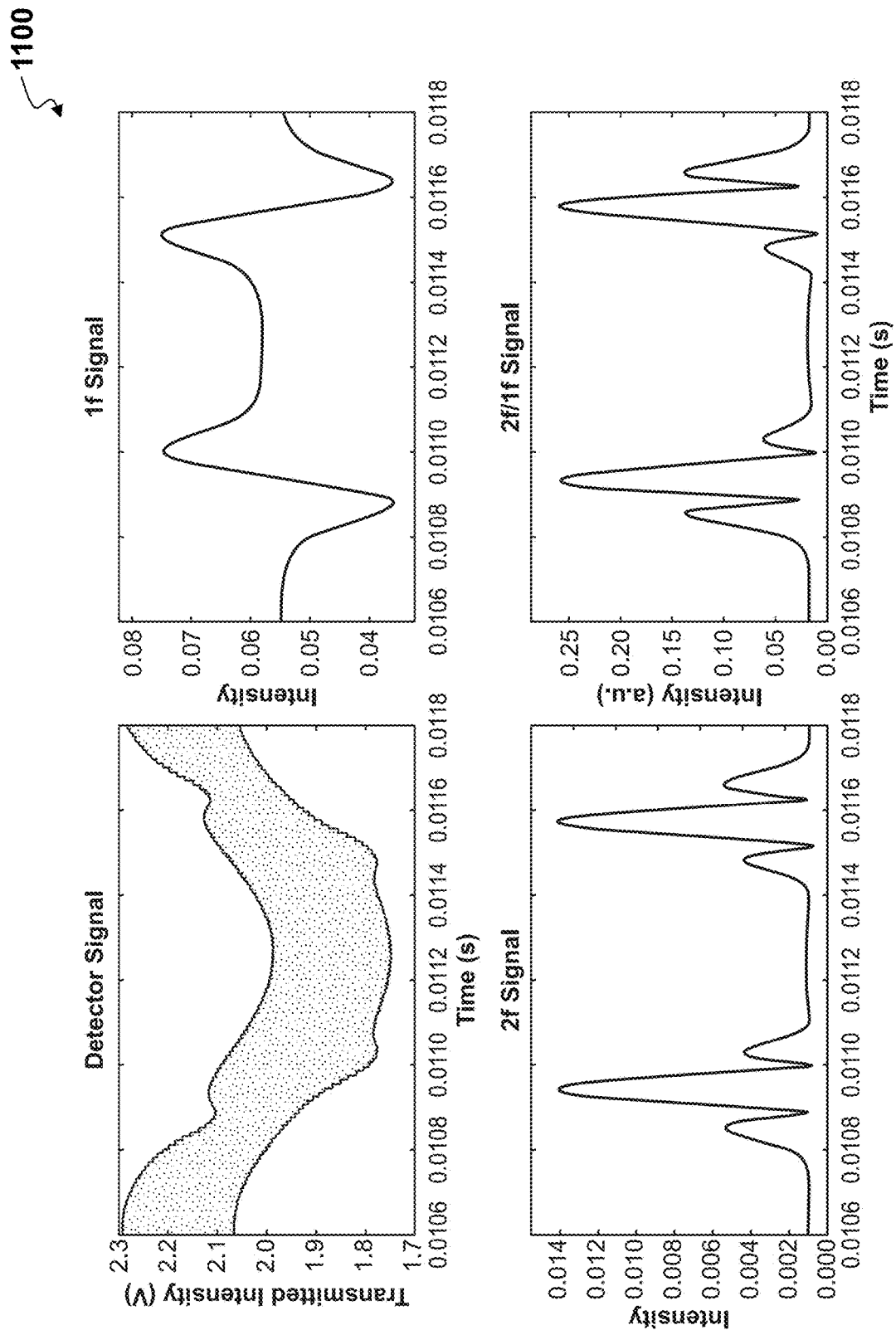
FIG. 11 depicts the use of wavelength modulated spectroscopy (WMS) a detector signal, 1f signal, 2f signal, and 2f/1f signal, according to one embodiment.

FIG. 11 depicts a detector signal, 1f signal, 2f signal, and 2f/1f signal 1100, according to one embodiment. These signals 1100 may be used to determine a concentration of two or more trace gases.

Figure 12:
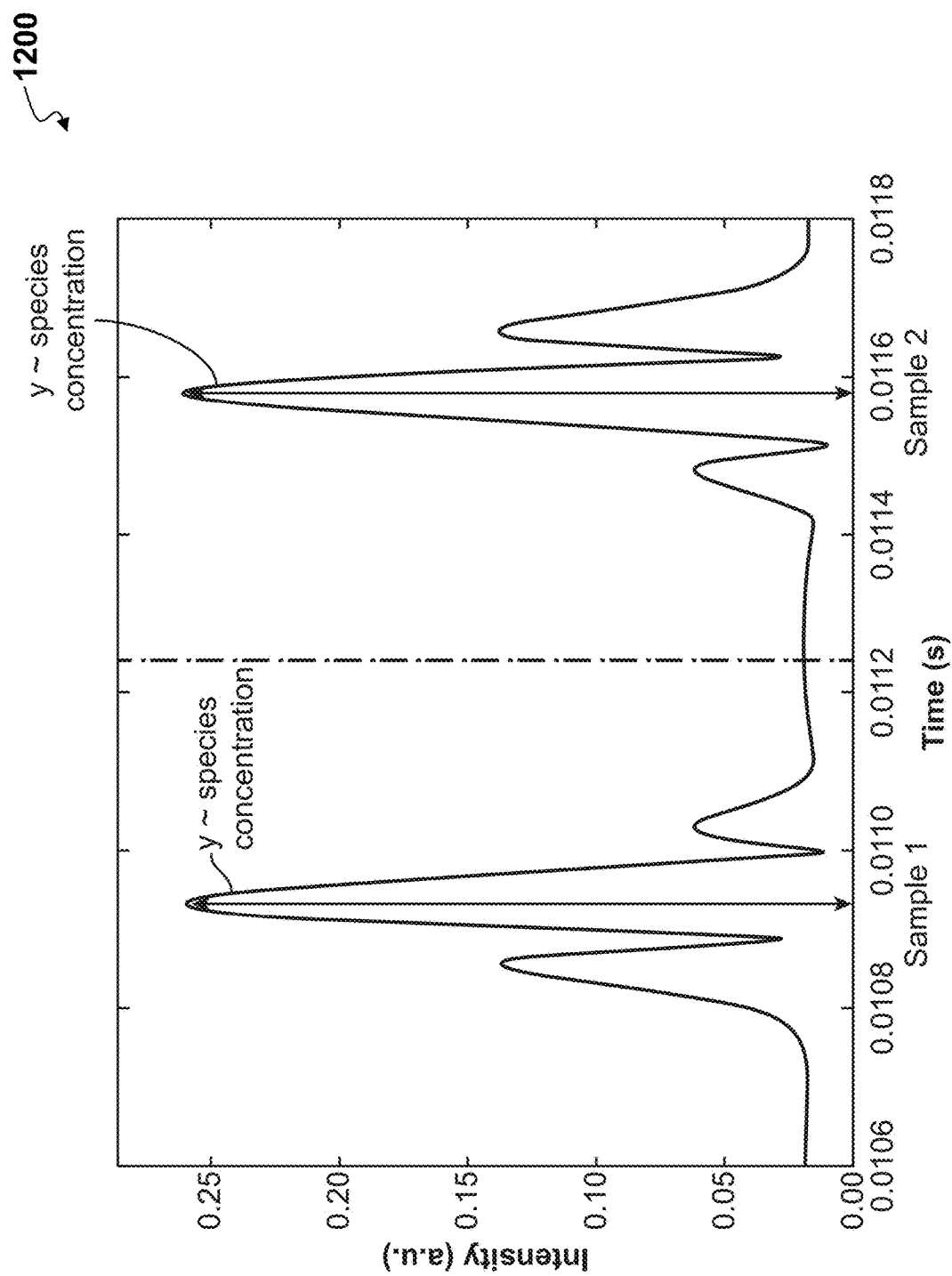
FIG. 12 depicts WMS-derived species concentration for two samples based on a peak wavelength, according to one embodiment.

FIG. 12 depicts species concentration 1200 for two samples based on a peak wavelength, according to one embodiment. The species concentration 1200 may be determined using the formula $\chi=y*a+b$. Where $\chi$ is species concentration, y is the signal measurement at the peak wavelength (in this case, a function of time due to scanning of laser current), and a and b are scalars determined through a calibration process.

Figure 13:
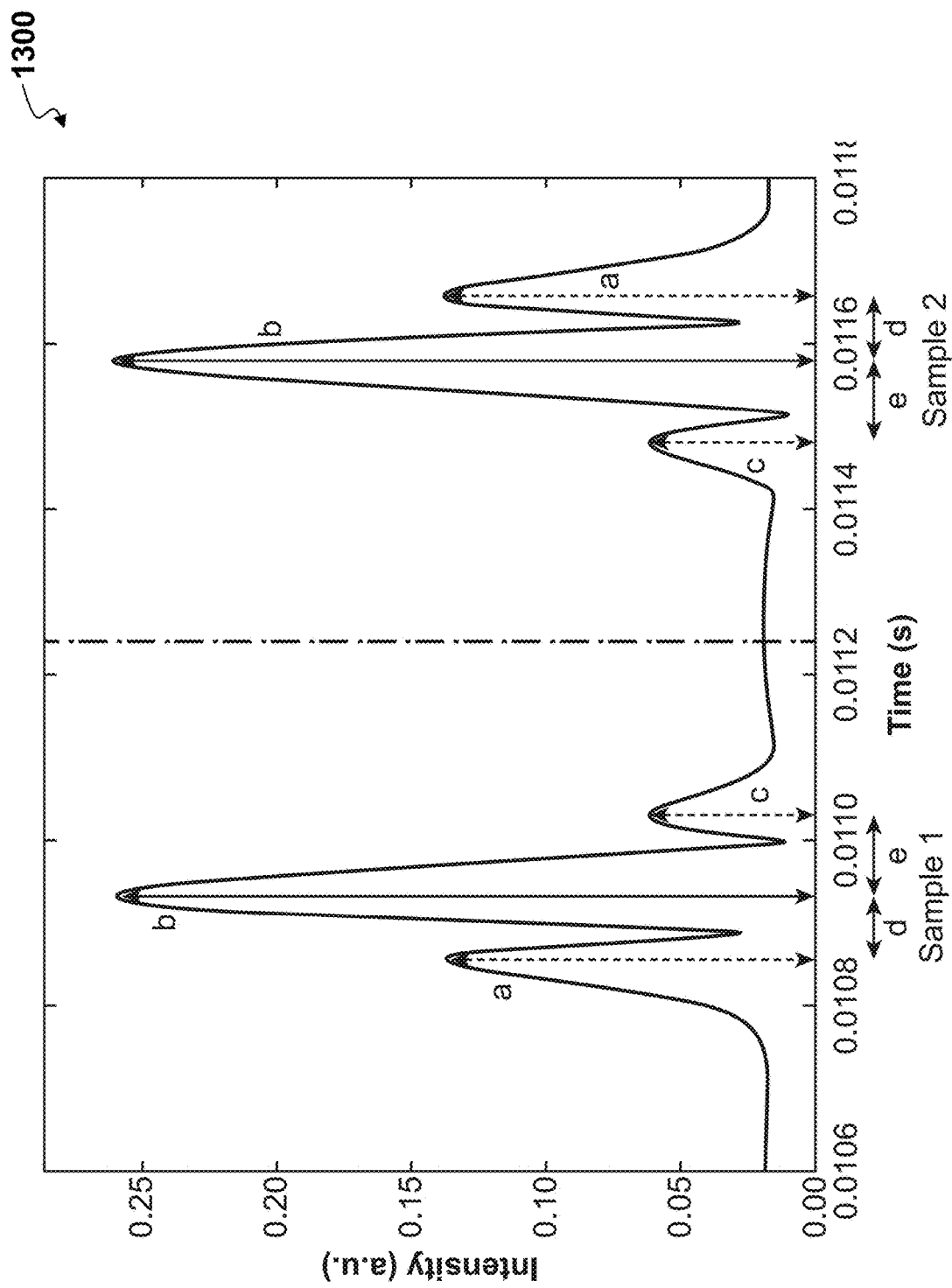
FIG. 13 depicts WMS-derived species concentration for two samples based on a look-up table, according to one embodiment.

FIG. 13 depicts species concentration 1300 for two samples based on a look-up table, according to one embodiment. One or more of the measurements (a,b,c,d,e) may be used to determine species concentration using a look-up table.

Figure 14:
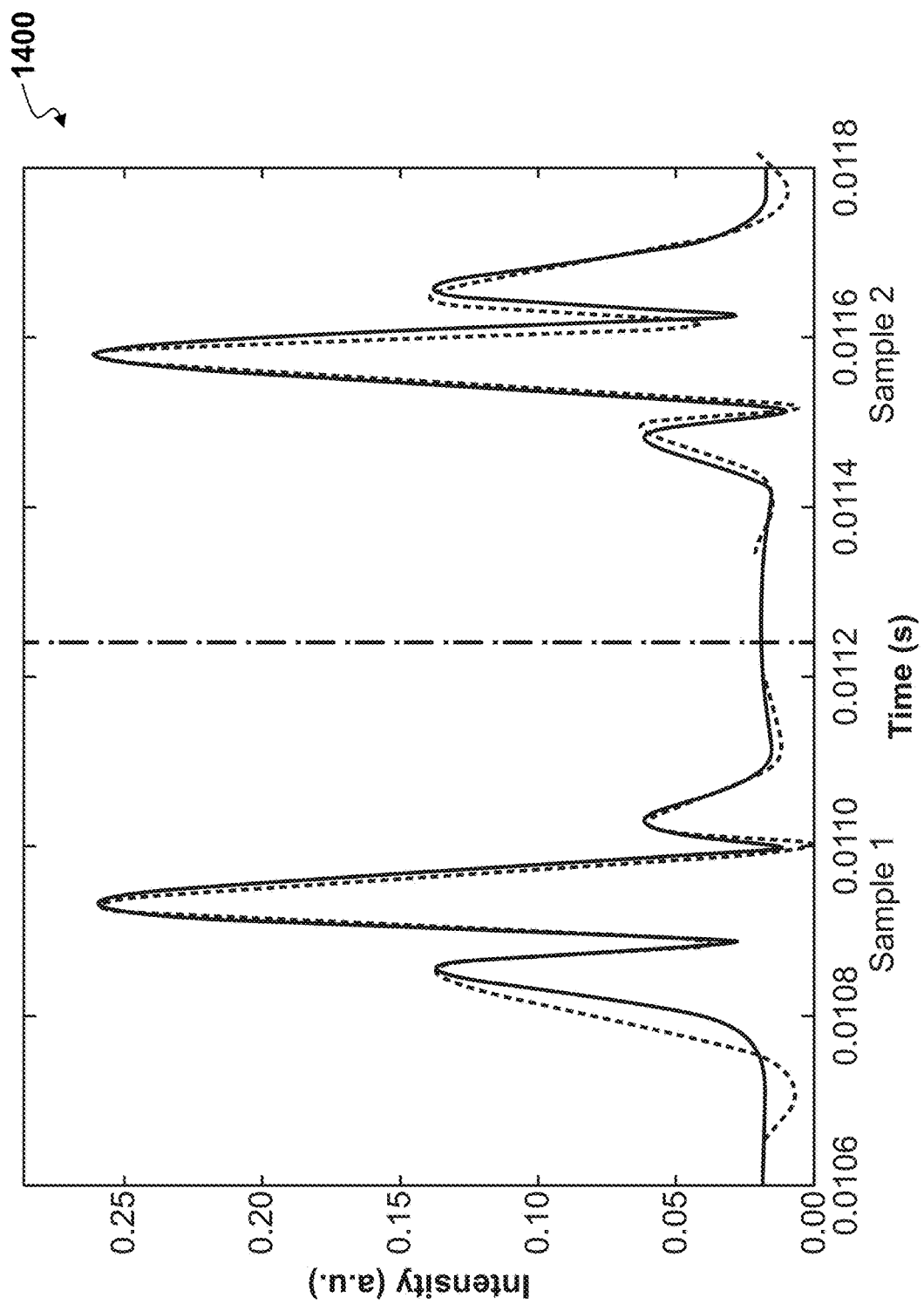
FIG. 14 depicts WMS-derived species concentration for two samples based on a non-linear regression and high-resolution transmission molecular absorption (HITRAN) database, according to one embodiment.

FIG. 14 depicts species concentration 1400 for two samples based on a non-linear regression and high-resolution transmission molecular absorption (HITRAN) database, according to one embodiment. A non-linear regression and HITRAN database may be used on each sample to determine a species concentration given temperature and pressure. In other embodiments, the system may assume a fixed temperature and pressure (e.g., standard temperature and pressure).

Figure 15:
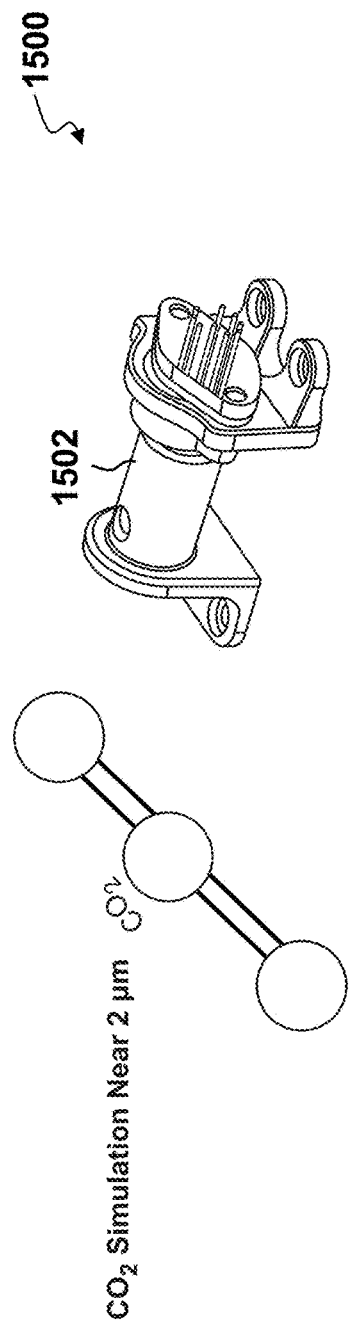
FIG. 15 depicts a carbon dioxide simulation near 2 m, according to one embodiment.
Figure 15:
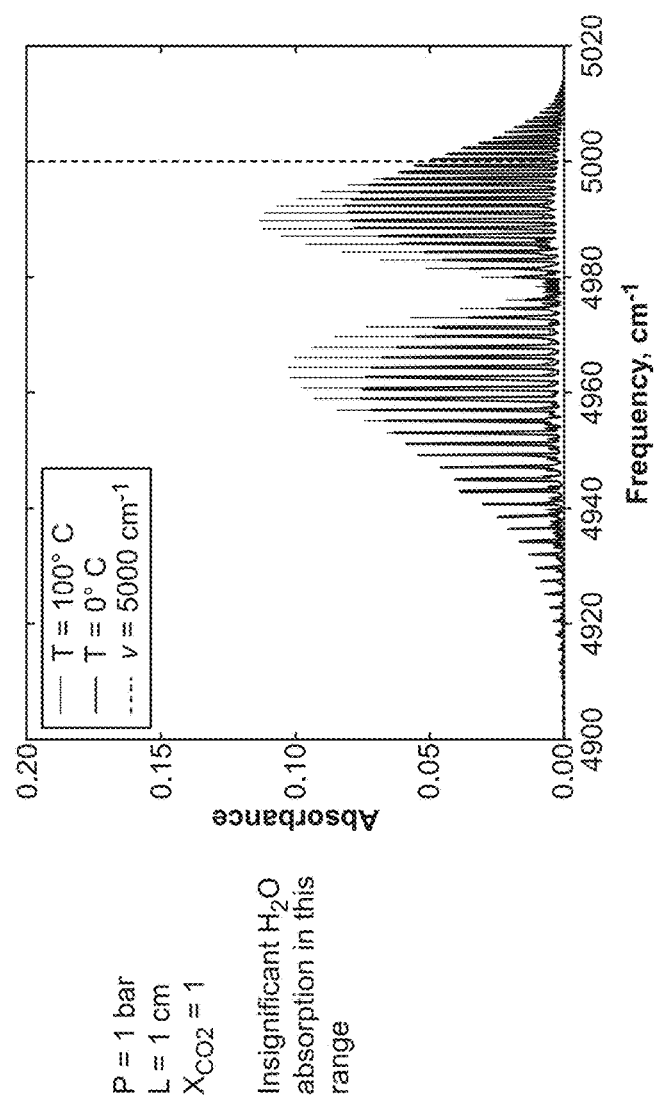

FIG. 15 depicts a carbon dioxide simulation near 2 m 1500, according to one embodiment. A high-sensitivity $CO_2$ sensor 1502 may be able to detect carbon dioxide at 1-2 ppm/s. In one embodiment, the $CO_2$ sensor 1502 may be a 1-inch cavity, such as Short Wavelength Infrared (SWIR) and/or midwave infrared (MWIR). The sensor 1502 may be optically simple, have a low interference, and may be highly sensitive. P may be 1 bar; L may be 1 cm; and $X_{CO2}$ may be 1. There may be insignificant $H_2O$ absorption in this range.

In one embodiment, the laser may be a Fabry-Perot interferometer (FPI) having an output wavelength of 2000 nm, an output power of 15 mW, an operating voltage of 2 V, an operating temperature of 25° C., and an operating current of 400 mA. In another embodiment, the laser may be a distributed feedback laser (DFB) having an output wavelength of 1900-2200 nm, an output power of 3 mW, an operating voltage of 2 V, an operating temperature of 25° C., and an operating current of 100 mA. Other laser types and specifications are possible and contemplated.

Figure 16:
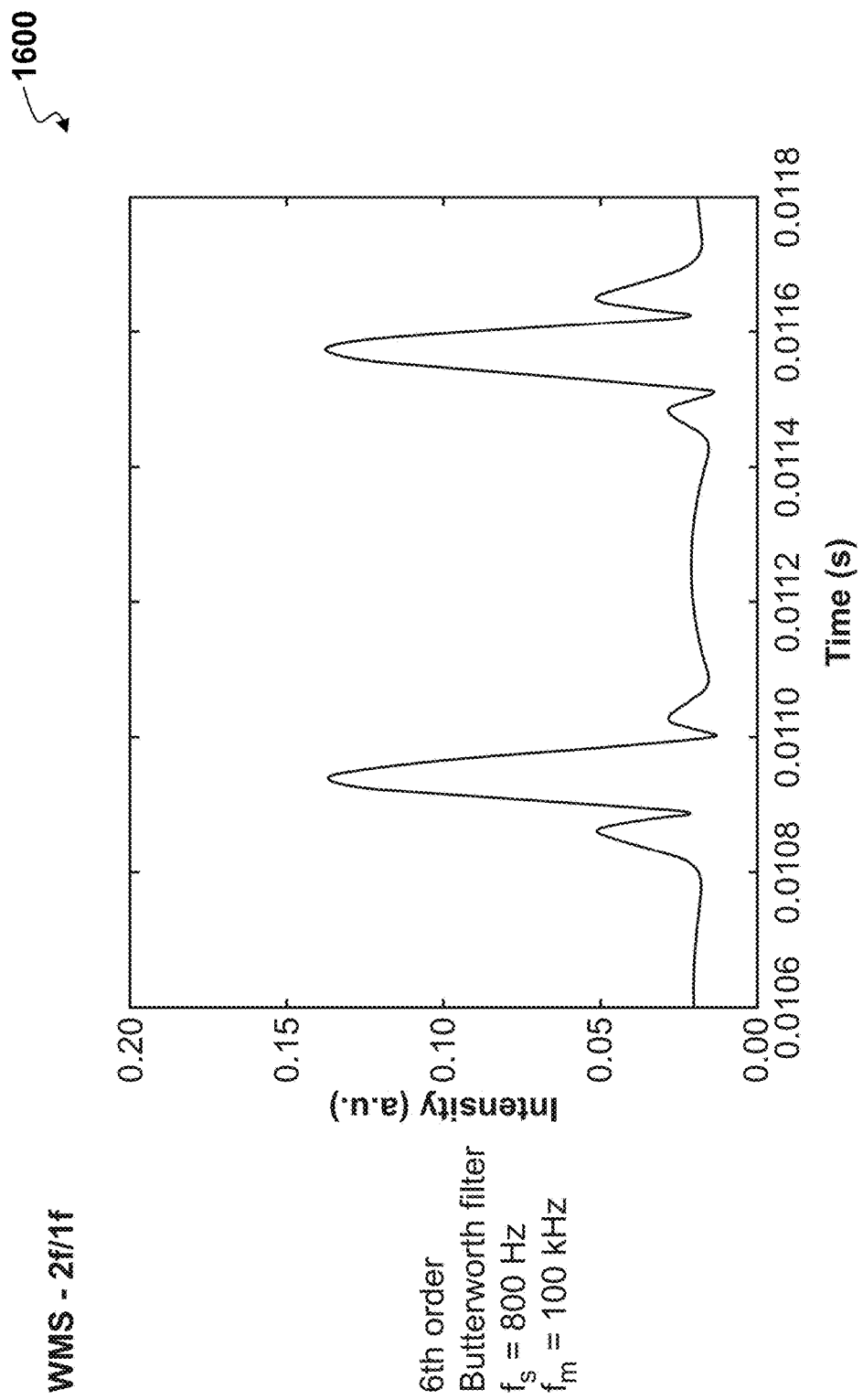
FIG. 16 depicts a graph showing WMS, according to one embodiment.

FIG. 16 depicts a graph 1600 showing wavelength-modulation spectroscopy (WMS), according to one embodiment. A Sixth Order Butterworth filter may have an fs of 800 Hz and an $f_m$ of 100 kHz.

Figure 17:
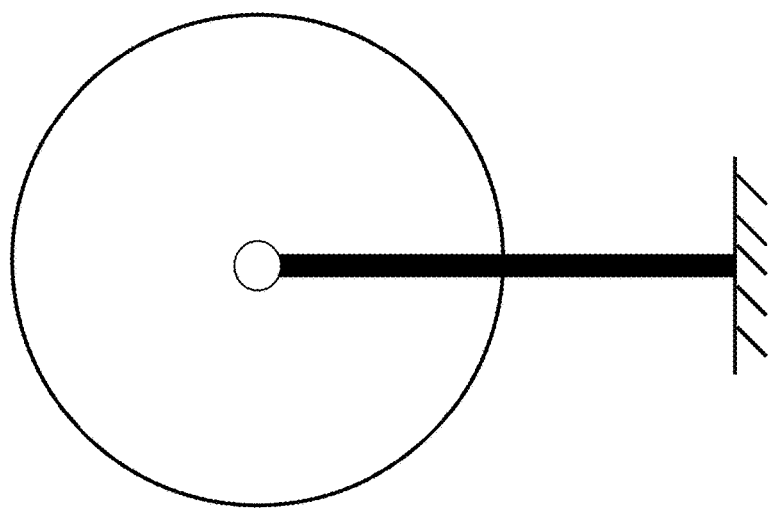
FIG. 17 depicts a downstream flare model, according to one embodiment.

FIG. 17 depicts a downstream flare model 1700, according to one embodiment. Inputs for flare calculations may include stoichiometric air and $CH_4$ at 20° C. and 1 atm. Constant temperature and enthalpy equilibration. Output Flare Conditions may include: T=2152 K; $Y_{N2}$=0.72, $X_{N2}$=0.70; $Y_{H2O}$=0.12, $X_{H2O}$=0.18; $Y_{CO2}$=0.13, $X_{CO2}$=0.08; $Y_{O2}$=0.01, $X_{O2}$=0.01; $Y_{CO}$=0.01, $X_{CO}$=0.01. The ambient air mass flow may be 10× the flare mass flow. Equilibrium Mass Fractions (Standard Air+$N_2$: 0.72+ 0.7628/10; $O_2$: 0.01+0.2047/10; $H_2O$: 0.12+0.0195/10; $CO_2$: 0.13+0.0039/10; Ar: 0.0091/10). Flare Conditions (mole fractions) T=100° C.; $X_{N2}$=0.74; $X_{H2O}$=0.11; $X_{CO2}$=0.12; $X_{O2}$=0.03.

Figure 18:
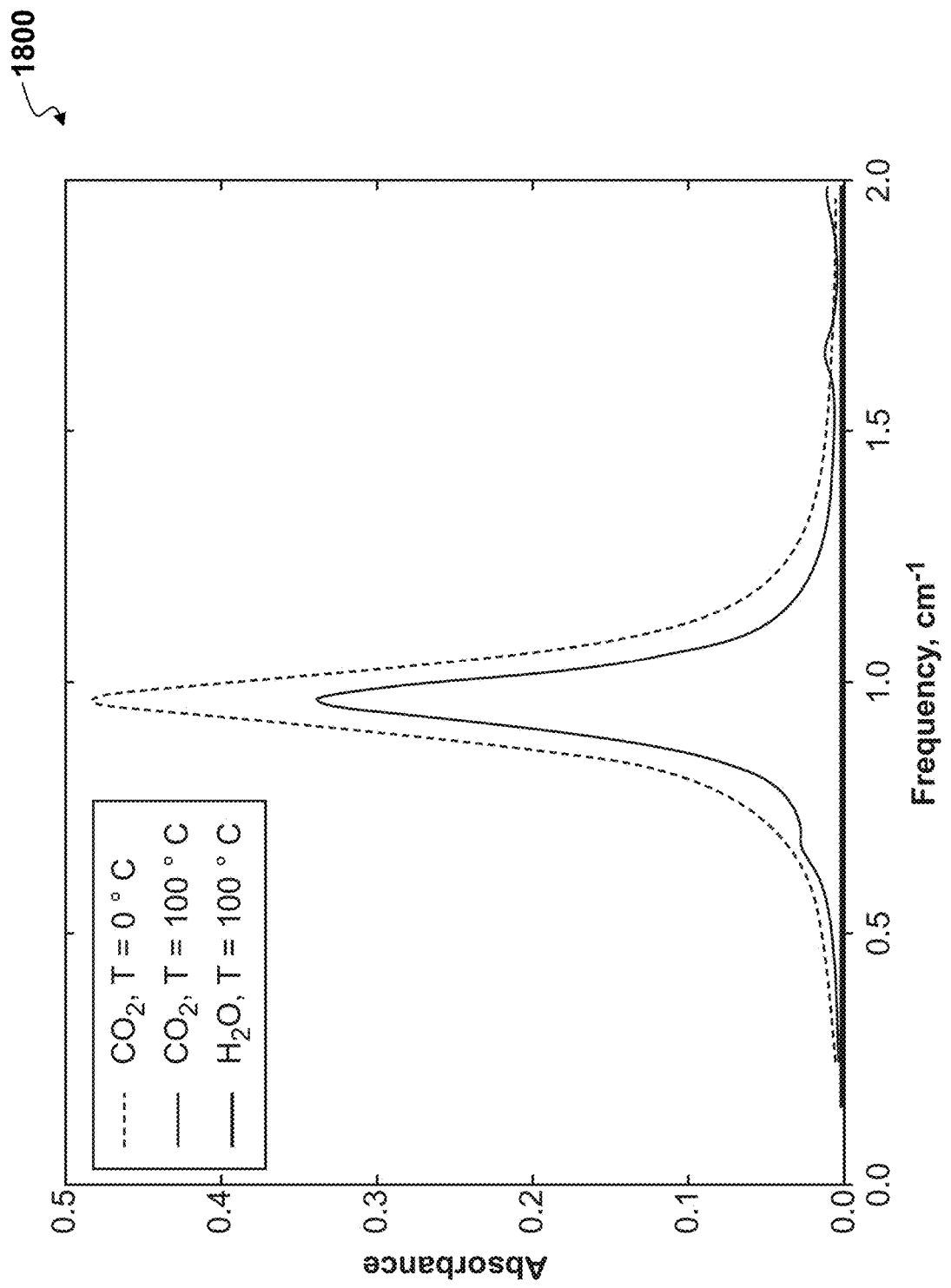
FIG. 18 depicts a data-based flare model, according to one embodiment.

FIG. 18 depicts a data based flare model 1800, according to one embodiment. Flare Conditions (mole fractions) T=100° C.; $X_{N2}$=0.756000; $X_{O2}$=0.200962; $X_{H2O}$=0.035; $X_{CO2}$=0.008; $X_{CH4}$=0.000028; $X_{CO}$=0.000010. Modeling (mole fractions) T=27° C.; $X_{N2}$=0.756; $X_{O2}$=0.201; $X_{H2O}$=0.035; $X_{CO2}$=0.008. Peak $H_2O$ absorbance=2.5× $10^{-4}$.

Figure 19:
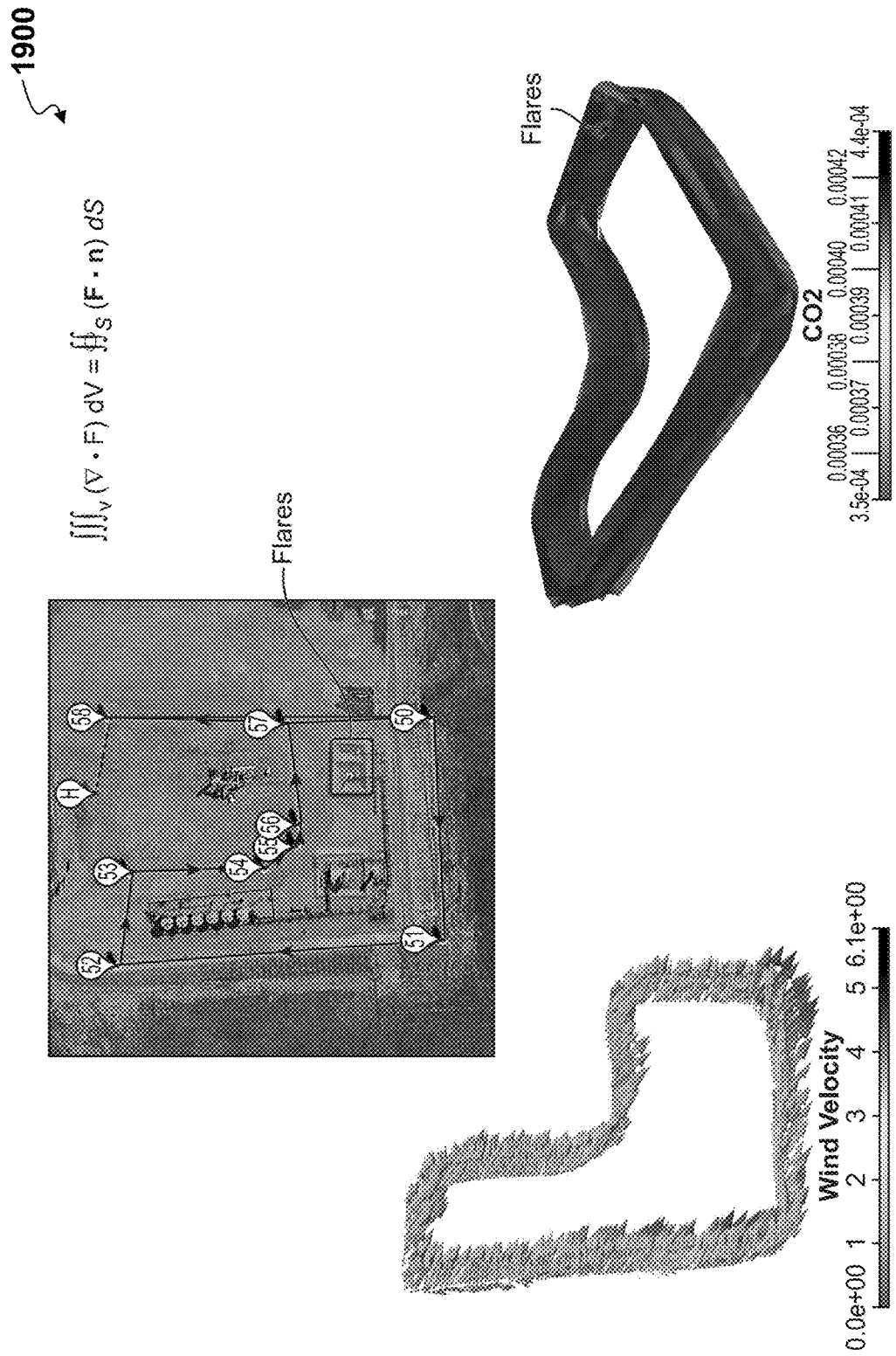
FIG. 19 depicts carbon dioxide concentrations from flares in a field test and the equation for going from a volume integral to a surface integral (Divergence theorem), according to one embodiment.

FIG. 19 depicts flares in a field test 1900, according to one embodiment. Flares are shown in the flux plane, showing elevated trace gas concentrations. The flares may have some uncombusted material ($CH_4$) as well as production of $CO_2$ and some other species. These additional gases may include $SO_x$, $NO_x$, CO, and the like. By measuring the concentration of $CO_2$ and methane in the surface surrounding the flares, the disclosed system and method can use the mathematical relationship to translate that into the volume and hence the amount of actual emissions from the source that has been completely surrounded.

Figure 20:
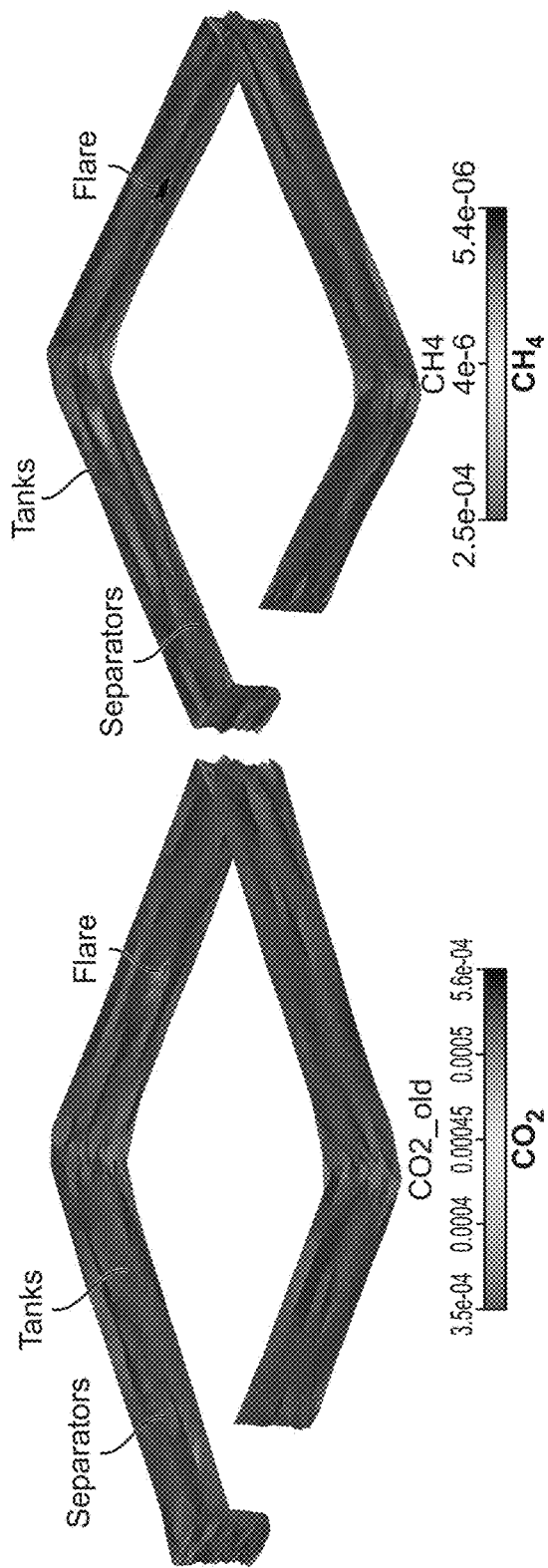
FIG. 20 depicts wellpad measurements of carbon dioxide and methane during separate data acquisition flights, according to one embodiment.

FIG. 20 depicts wellpad measurements of carbon dioxide and methane 2000, according to one embodiment. Tanks, flares, and separators are shown in the elevated trace gas concentrations of methane and carbon dioxide.

Figure 21:
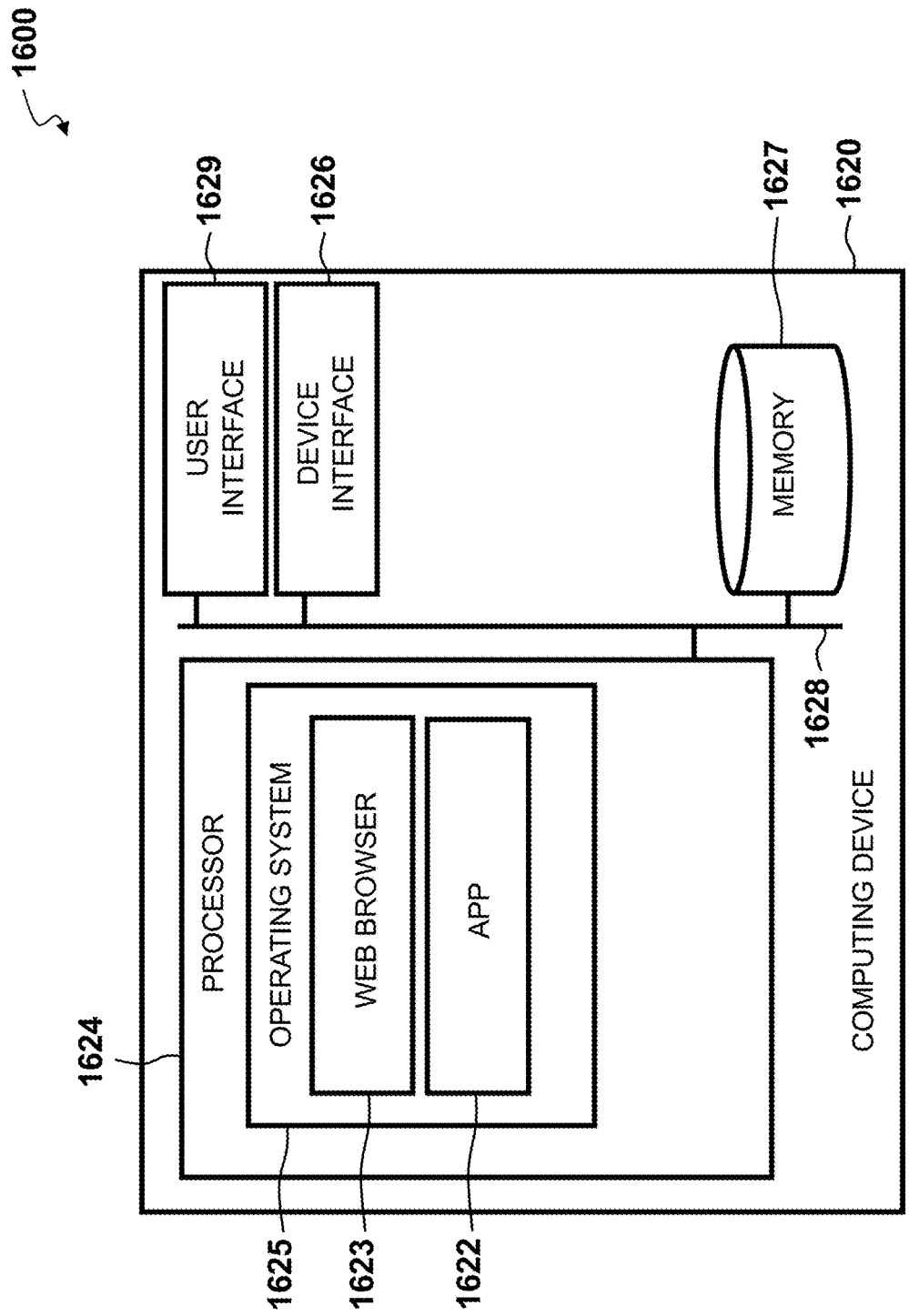
FIG. 21 illustrates an example top-level functional block diagram of a computing device embodiment, according to one embodiment.

FIG. 21 illustrates an example of a top-level functional block diagram of a computing device embodiment 1600. The example operating environment is shown as a computing device 1620 comprising a processor 1624, such as a central processing unit (CPU), addressable memory 1627, an external device interface 1626, e.g., an optional universal serial bus port and related processing, and/or an Ethernet port and related processing, and an optional user interface 1629, e.g., an array of status lights and one or more toggle switches, and/or a display, and/or a keyboard and/or a pointer-mouse system and/or a touch screen. Optionally, the addressable memory may, for example, be: flash memory, eprom, and/or a disk drive or other hard drive. These elements may be in communication with one another via a data bus 1628. In some embodiments, via an operating system 1625 such as one supporting a web browser 1623 and applications 1622, the processor 1624 may be configured to execute steps of a process establishing a communication channel and processing according to the embodiments described above.

System embodiments include computing devices such as a server computing device, a buyer computing device, and a seller computing device, each comprising a processor and addressable memory and in electronic communication with each other. The embodiments provide a server computing device that may be configured to: register one or more buyer computing devices and associate each buyer computing device with a buyer profile; register one or more seller computing devices and associate each seller computing device with a seller profile; determine search results of one or more registered buyer computing devices matching one or more buyer criteria via a seller search component. The service computing device may then transmit a message from the registered seller computing device to a registered buyer computing device from the determined search results and provide access to the registered buyer computing device of a property from the one or more properties of the registered seller via a remote access component based on the transmitted message and the associated buyer computing device; and track movement of the registered buyer computing device in the accessed property via a viewer tracking component. Accordingly, the system may facilitate the tracking of buyers by the system and sellers once they are on the property and aid in the seller's search for finding buyers for their property. The figures described below provide more details about the implementation of the devices and how they may interact with each other using the disclosed technology.

Figure 22:
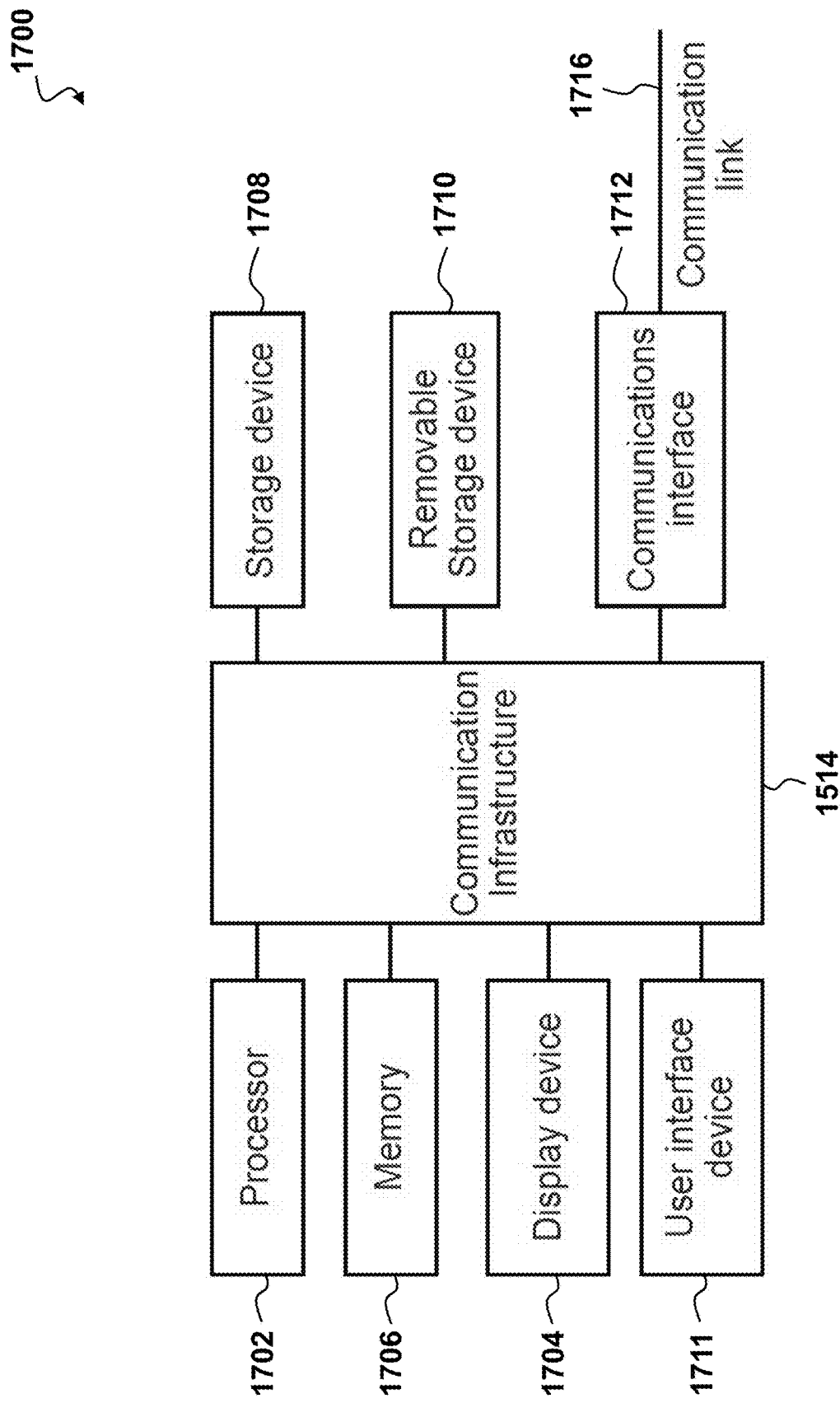
FIG. 22 shows a high-level block diagram and process of a computing system for implementing an embodiment of the system and process, according to one embodiment.

FIG. 22 is a high-level block diagram 1700 showing a computing system comprising a computer system useful for implementing an embodiment of the system and process, disclosed herein. Embodiments of the system may be implemented in different computing environments. The computer system includes one or more processors 1702, and can further include an electronic display device 1704 (e.g., for displaying graphics, text, and other data), a main memory 1706 (e.g., random access memory (RAM)), storage device 1708, a removable storage device 1710 (e.g., removable storage drive, a removable memory module, a magnetic tape drive, an optical disk drive, a computer readable medium having stored therein computer software and/or data), user interface device 1711 (e.g., keyboard, touch screen, keypad, pointing device), and a communication interface 1712 (e.g., modem, a network interface (such as an Ethernet card), a communications port, or a PCMCIA slot and card). The communication interface 1712 allows software and data to be transferred between the computer system and external devices. The system further includes a communications infrastructure 1714 (e.g., a communications bus, cross-over bar, or network) to which the aforementioned devices/modules are connected as shown.

Information transferred via communications interface 1714 may be in the form of signals such as electronic, electromagnetic, optical, or other signals capable of being received by communications interface 1714, via a communication link 1716 that carries signals and may be implemented using wire or cable, fiber optics, a phone line, a cellular/mobile phone link, an radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 1712. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 23:
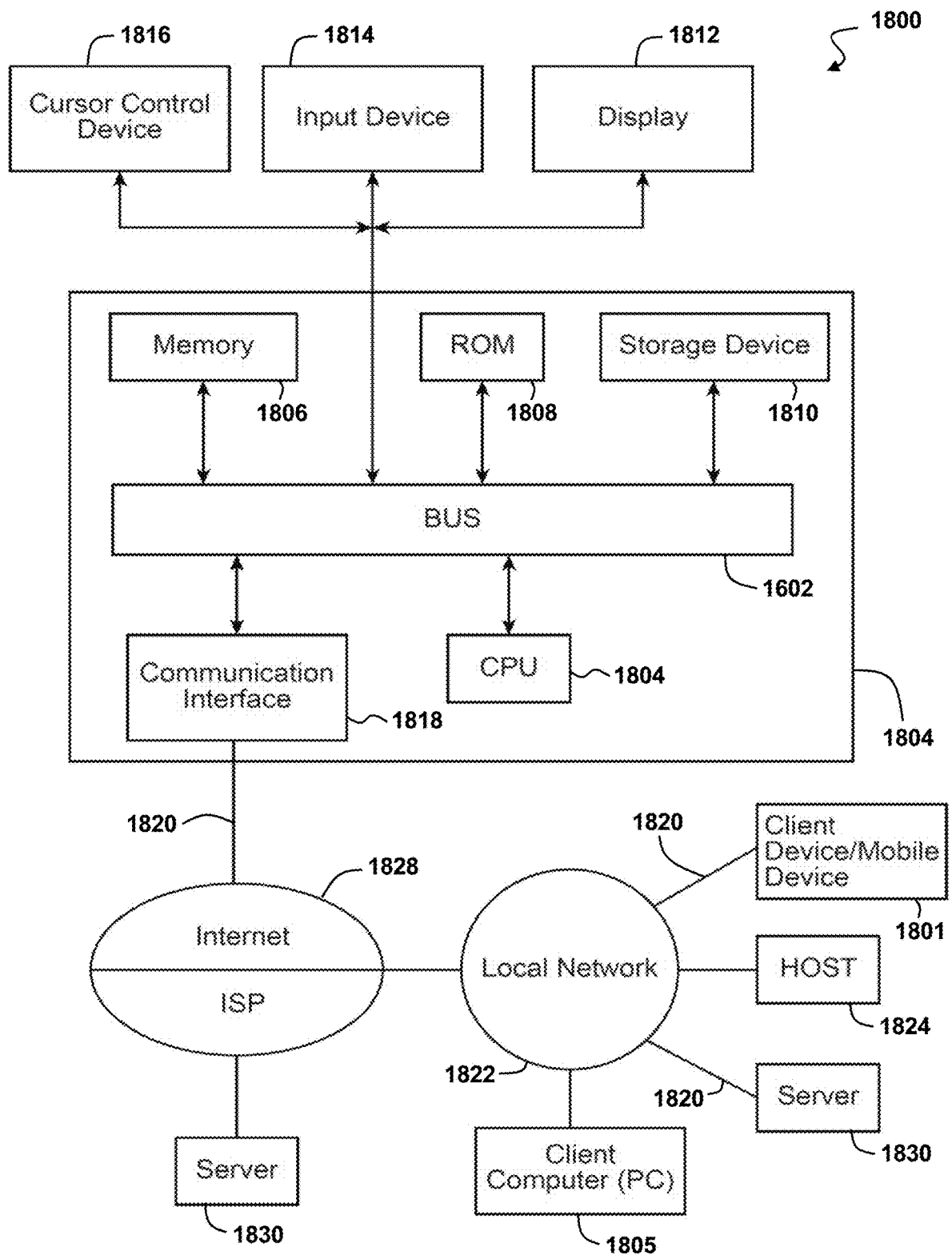
FIG. 23 shows a block diagram and process of an exemplary system in which an embodiment may be implemented, according to one embodiment.

FIG. 23 shows a block diagram of an example system 1800 in which an embodiment may be implemented. The system 1800 includes one or more client devices 1801 such as consumer electronics devices, connected to one or more server computing systems 1830. A server 1830 includes a bus 1802 or other communication mechanism for communicating information, and a processor (CPU) 1804 coupled with the bus 1802 for processing information. The server 1830 also includes a main memory 1806, such as a random access memory (RAM) or other dynamic storage device, coupled to the bus 1802 for storing information and instructions to be executed by the processor 1804. The main memory 1806 also may be used for storing temporary variables or other intermediate information during execution or instructions to be executed by the processor 1804. The server computer system 1830 further includes a read only memory (ROM) 1808 or other static storage device coupled to the bus 1802 for storing static information and instructions for the processor 1804. A storage device 1810, such as a magnetic disk or optical disk, is provided and coupled to the bus 1802 for storing information and instructions. The bus 1802 may contain, for example, thirty-two address lines for addressing video memory or main memory 1806. The bus 1802 can also include, for example, a 32-bit data bus for transferring data between and among the components, such as the CPU 1804, the main memory 1806, video memory and the storage 1810. Alternatively, multiplex data/address lines may be used instead of separate data and address lines.

The server 1830 may be coupled via the bus 1802 to a display 1812 for displaying information to a computer user. An input device 1814, including alphanumeric and other keys, is coupled to the bus 1802 for communicating information and command selections to the processor 1804. Another type or user input device comprises cursor control 1816, such as a mouse, a trackball, or cursor direction keys for communicating direction information and command selections to the processor 1804 and for controlling cursor movement on the display 1812.

According to one embodiment, the functions are performed by the processor 1804 executing one or more sequences of one or more instructions contained in the main memory 1806. Such instructions may be read into the main memory 1806 from another computer-readable medium, such as the storage device 1810. Execution of the sequences of instructions contained in the main memory 1806 causes the processor 1804 to perform the process steps described herein. One or more processors in a multi-processing arrangement may also be employed to execute the sequences of instructions contained in the main memory 1806. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 1804 for execution. Such a medium may take many forms, including but not limited to, non-volatile media, volatile media, and transmission media. Non-volatile media includes, for example, optical or magnetic disks, such as the storage device 1810. Volatile media includes dynamic memory, such as the main memory 1806. Transmission media includes coaxial cables, copper wire and fiber optics, including the wires that comprise the bus 1802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 1804 for execution. For example, the instructions may initially be carried on a magnetic disk of a remote computer. The remote computer can load the instructions into its dynamic memory and send the instructions over a telephone line using a modem. A modem local to the server 1830 can receive the data on the telephone line and use an infrared transmitter to convert the data to an infrared signal. An infrared detector coupled to the bus 1802 can receive the data carried in the infrared signal and place the data on the bus 1802. The bus 1802 carries the data to the main memory 1806, from which the processor 1804 retrieves and executes the instructions. The instructions received from the main memory 1806 may optionally be stored on the storage device 1810 either before or after execution by the processor 1804.

The server 1830 also includes a communication interface 1818 coupled to the bus 1802. The communication interface 1818 provides a two-way data communication coupling to a network link 1820 that is connected to the world wide packet data communication network now commonly referred to as the Internet 1828. The Internet 1828 uses electrical, electromagnetic or optical signals that carry digital data streams. The signals through the various networks and the signals on the network link 1820 and through the communication interface 1818, which carry the digital data to and from the server 1830, are exemplary forms or carrier waves transporting the information.

In another embodiment of the server 1830, interface 1818 is connected to a network 1822 via a communication link 1820. For example, the communication interface 1818 may be an integrated services digital network (ISDN) card or a modem to provide a data communication connection to a corresponding type of telephone line, which can comprise part of the network link 1820. As another example, the communication interface 1818 may be a local area network (LAN) card to provide a data communication connection to a compatible LAN. Wireless links may also be implemented. In any such implementation, the communication interface 1818 sends and receives electrical electromagnetic or optical signals that carry digital data streams representing various types of information.

The network link 1820 typically provides data communication through one or more networks to other data devices. For example, the network link 1820 may provide a connection through the local network 1822 to a host computer 1824 or to data equipment operated by an Internet Service Provider (ISP). The ISP in turn provides data communication services through the Internet 1828. The local network 1822 and the Internet 1828 both use electrical, electromagnetic or optical signals that carry digital data streams. The signals through the various networks and the signals on the network link 1820 and through the communication interface 1818, which carry the digital data to and from the server 1830, are exemplary forms or carrier waves transporting the information.

The server 1830 can send/receive messages and data, including e-mail, program code, through the network, the network link 1820 and the communication interface 1818. Further, the communication interface 1818 can comprise a USB/Tuner and the network link 1820 may be an antenna or cable for connecting the server 1830 to a cable provider, satellite provider or other terrestrial transmission system for receiving messages, data and program code from another source.

The example versions of the embodiments described herein may be implemented as logical operations in a distributed processing system such as the system 1800 including the servers 1830. The logical operations of the embodiments may be implemented as a sequence of steps executing in the server 1830, and as interconnected machine modules within the system 1800. The implementation is a matter of choice and can depend on performance of the system 1800 implementing the embodiments. As such, the logical operations constituting said example versions of the embodiments are referred to for e.g., as operations, steps or modules.

Similar to a server 1830 described above, a client device 1801 can include a processor, memory, storage device, display, input device and communication interface (e.g., e-mail interface) for connecting the client device to the Internet 1828, the ISP, or LAN 1822, for communication with the servers 1830.

The system 1800 can further include computers (e.g., personal computers, computing nodes) 1805 operating in the same manner as client devices 1801, where a user can utilize one or more computers 1805 to manage data in the server 1830.

Figure 24:
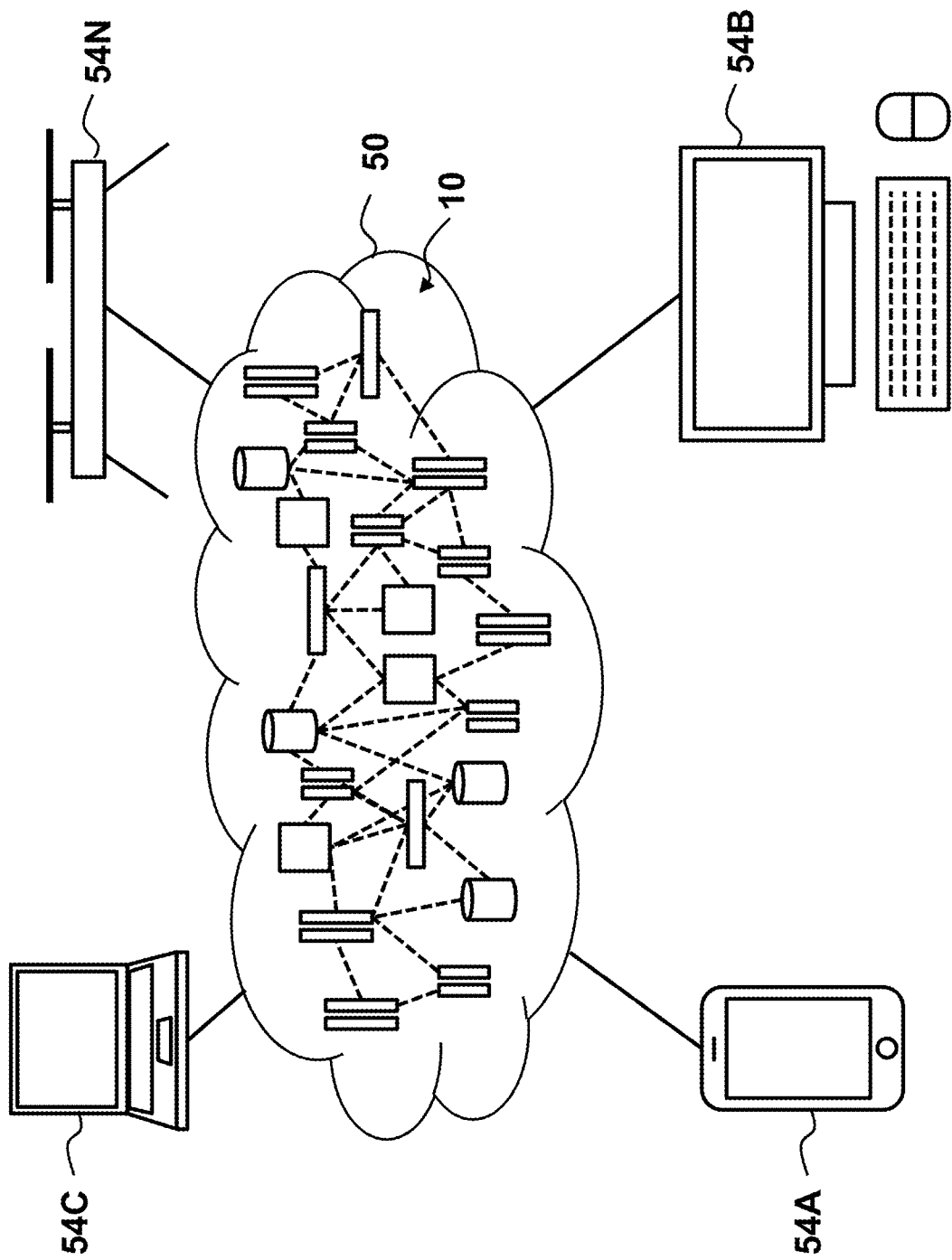
FIG. 24 depicts a cloud-computing environment for implementing an embodiment of the system and process disclosed herein, according to one embodiment.

Referring now to FIG. 24, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smart watch, set-top box, video game system, tablet, mobile computing device, or cellular telephone 54A, desktop computer 54B, laptop computer 54C, and/or unmanned aerial system (UAS) 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 24 are intended to be illustrative only and that computing nodes 10 and cloud computing environment 50 can communicate with any type of computerized device over any type of network and/or network addressable connection (e.g., using a web browser).

Figure 25:
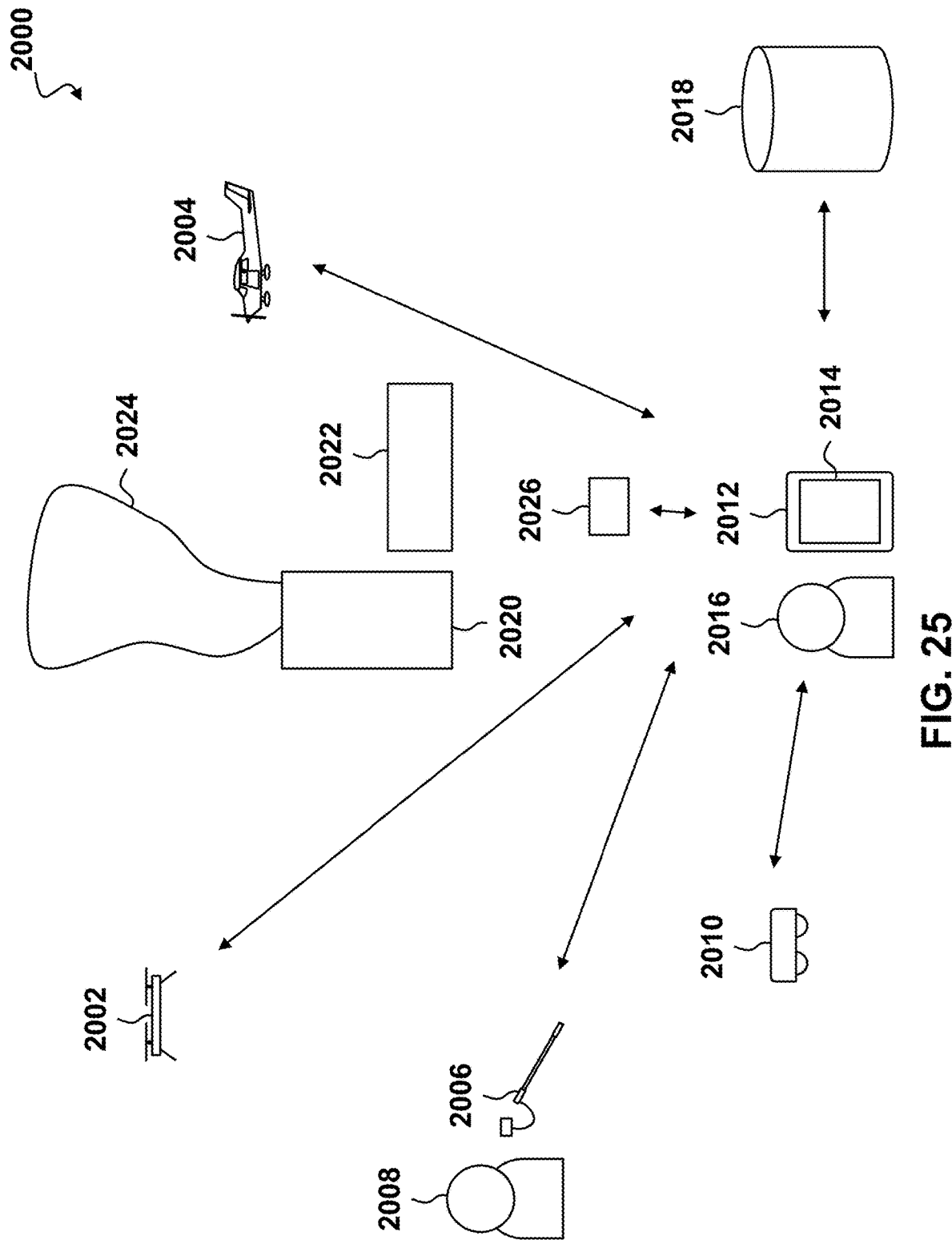
FIG. 25 depicts a system for detecting trace gases, according to one embodiment.

FIG. 25 depicts a system 2000 for detecting trace gases, according to one embodiment. The system may include one or more trace gas sensors located in one or more vehicles 2002, 2004, 2006, 2010. The one or more trace gas sensors may detect elevated trace gas concentrations from one or more potential gas sources 2020, 2022, such as a holding tank, pipeline, or the like. The potential gas sources 2020, 2022 may be part of a large facility, a small facility, or any location. The potential gas sources 2020, 2022 may be clustered and/or disposed distal from one another. The one or more trace gas sensors may be used to detect and quantify leaks of toxic gases, e.g., hydrogen disulfide, or environmentally damaging gases, e.g., methane, sulfur dioxide) in a variety of industrial and environmental contexts. Detection and quantification of these leaks are of interest to a variety of industrial operations, such as oil and gas, chemical production, and painting. Detection and quantification of leaks is also of value to environmental regulators for assessing compliance and for mitigating environmental and safety risks. In some embodiments, the at least one trace gas sensor may be configured to detect methane. In other embodiments, the at least one trace gas sensor may be configured to detect sulfur oxide, such as SO, SO2, SO3, S7O2, S6O2, S2O2, and the like. A trace gas leak 2024 may be present in a potential gas source 2020. The one or more trace gas sensors may be used to identify the trace gas leak 2024 and/or the source 2020 of the trace gas leak 2024 so that corrective action may be taken.

The one or more vehicles 2002, 2004, 2006, 2010 may include an unmanned aerial vehicle (UAV) 2002, an aerial vehicle 2004, a handheld device 2006, and a ground vehicle 2010. In some embodiments, the UAV 2002 may be a quadcopter or other device capable of hovering, making sharp turns, and the like. In other embodiments, the UAV 2002 may be a winged aerial vehicle capable of extended flight time between missions. The UAV 2002 may be autonomous or semi-autonomous in some embodiments. In other embodiments, the UAV 2002 may be manually controlled by a user. The aerial vehicle 2004 may be a manned vehicle in some embodiments. The handheld device 2006 may be any device having one or more trace gas sensors operated by a user 2008. In one embodiment, the handheld device 2006 may have an extension for keeping the one or more trace gas sensors at a distance from the user 2008. The ground vehicle 2010 may have wheels, tracks, and/or treads in one embodiment. In other embodiments, the ground vehicle 2010 may be a legged robot. In some embodiments, the ground vehicle 2010 may be used as a base station for one or more UAVs 2002. In some embodiments, one or more aerial devices, such as the UAV 2002, a balloon, or the like, may be tethered to the ground vehicle 2010. In some embodiments, one or more trace gas sensors may be located in one or more stationary monitoring devices 2026. The one or more stationary monitoring devices may be located proximate one or more potential gas sources 2020, 2022. In some embodiments, the one or more stationary monitoring devices may be relocated.

The one or more vehicles 2002, 2004, 2006, 2010 and/or stationary monitoring devices 2026 may transmit data including trace gas data to a ground control station (GCS) 2012. The GCS may include a display 2014 for displaying the trace gas concentrations to a GCS user 2016. The GCS user 2016 may be able to take corrective action if a gas leak 2024 is detected, such as by ordering a repair of the source 2020 of the trace gas leak. The GCS user 2016 may be able to control movement of the one or more vehicles 2002, 2004, 2006, 2010 in order to confirm a presence of a trace gas leak in some embodiments.

In some embodiments, the GCS 2012 may transmit data to a cloud server 2018. In some embodiments, the cloud server 2018 may perform additional processing on the data. In some embodiments, the cloud server 2018 may provide third party data to the GCS 2012, such as wind speed, temperature, pressure, weather data, or the like.

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention herein disclosed by way of examples should not be limited by the particular disclosed embodiments described above.

What is claimed is:

1. A system comprising:
   an optical cavity;
   a plurality of light sources configured to emit at least one of: a specified wavelength of light and a band of wavelengths of light into the optical cavity such that the emitted light travels one or more path lengths over one or more distances from the light source, wherein the plurality of light sources are at least one of: tuned to a first trace gas species and a second trace gas species, and tuned to a continuous wavelength shifting between the first trace gas species and the second trace gas species, wherein the plurality of light sources are associated with the optical cavity; and
   one or more photovoltaic detectors configured to receive the emitted light that has traveled over the one or more path lengths, wherein the one or more photovoltaic detectors are configured to detect the first trace gas species and the second trace gas species, and wherein when the plurality of light sources are tuned to the continuous wavelength, a detected first trace gas species is hydrocarbon and a detected second trace gas species is a gas other than hydrocarbon.

2. The system of claim 1, wherein the one or more optical cavities comprise at least one mirror.

3. The system of claim 1, wherein the one or more optical cavities comprise at least two mirrors.

4. The system of claim 1, wherein the one or more light sources comprise at least one of: a laser, a light-emitting diode (LED), a superluminescent diode (SLD), and a lamp.

5. The system of claim 1, wherein the first trace gas species comprises at least one of: methane and carbon dioxide and the second trace gas species comprises at least one of: methane and carbon dioxide.

6. The system of claim 1, wherein the one or more optical cavities comprise two optical cavities.

7. The system of claim 1, wherein the one or more light sources comprise two light sources.

8. The system of claim 1, wherein the one or more photovoltaic detectors comprise two photovoltaic detectors.

9. A system comprising:
   an optical cavity;
   a plurality of light sources configured to emit at least one of: a specified wavelength of light and a band of wavelengths of light into the optical cavity such that the emitted light travels one or more path lengths over one or more distances from the plurality of light sources, wherein the plurality of light sources are at least one of: tuned to a first trace gas species and a second trace gas species, and tuned to a continuous wavelength between a first trace gas species and a second trace gas species, wherein the plurality of light sources are associated with the optical cavity;
   and
   a photovoltaic detector configured to receive the emitted light that has traveled over the one or more path lengths, wherein the photovoltaic detector is configured to detect the first trace gas species and the second trace gas species, and wherein when the plurality of light sources are turned to the continuous wavelength a detected first trace gas species is hydrocarbon and a detected second trace gas species is a gas other than hydrocarbon.

10. The system of claim 9, further comprising:
    one or more mirrors disposed in the optical cavity.

11. The system of claim 9, wherein the one or more light sources comprise at least one of: a laser, a light-emitting diode (LED), a superluminescent diode (SLD), and a lamp;

wherein the first trace gas species comprises at least one of: methane and carbon dioxide; and wherein the second trace gas species comprises at least one of: methane and carbon dioxide.

12. A system comprising:
   an optical cavity;
   a plurality of light sources configured to emit at least one of: a specified wavelength of light and a band of wavelengths of light into the optical cavity such that the emitted light travels one or more path lengths over one or more distances from the light source, wherein each light source of the plurality of light sources is tuned to at least one of: a plurality of different trace gas species and a continuous wavelength shifting between the plurality of different trace gas species, wherein the plurality of light sources are associated with the optical cavity; and
   a photovoltaic detector configured to receive the emitted light that has traveled over the one or more path lengths, wherein the photovoltaic detector is configured to detect the plurality of different trace gas species, and wherein when the plurality of light sources are tuned to the continuous wavelength, a detected first trace gas species of the plurality of different trace gas species is hydrocarbon and a detected second trace gas species of the plurality of different trace gas species is a gas other than hydrocarbon.

* * * * *